US012201731B2

(12) United States Patent
Blaesi et al.

(10) Patent No.: US 12,201,731 B2
(45) Date of Patent: Jan. 21, 2025

(54) METHOD FOR 3D-MICRO-PATTERNING

(71) Applicant: Aron H. Blaesi, Cambridge, MA (US)

(72) Inventors: Aron H. Blaesi, Cambridge, MA (US);
Nannaji Saka, Cambridge, MA (US)

(73) Assignee: Aron H. Blaesi, Cambridge, MA (US)

( * ) Notice: Subject to any disclaimer, the term of this patent is extended or adjusted under 35 U.S.C. 154(b) by 830 days.

(21) Appl. No.: 17/237,034

(22) Filed: Apr. 21, 2021

(65) Prior Publication Data
US 2021/0290559 A1 Sep. 23, 2021

Related U.S. Application Data

(63) Continuation of application No. PCT/US2021/022860, filed on Mar. 17, 2021.

(60) Provisional application No. 63/158,870, filed on Mar. 9, 2021, provisional application No. 63/085,893, filed on Sep. 30, 2020, provisional application No. 62/991,052, filed on Mar. 17, 2020.

(51) Int. Cl.
*A61K 9/70* (2006.01)
*A61J 3/00* (2006.01)

(52) U.S. Cl.
CPC .. *A61K 9/70* (2013.01); *A61J 3/00* (2013.01)

(58) Field of Classification Search
CPC ...... B29C 45/16; B29C 45/1603–1604; B29C 64/10; B29C 64/106; B29C 64/118; B29C 64/20; B29C 64/205; B29C 64/209; B29C 64/227; B29C 64/386; B33Y 30/00; B33Y 30/386; B33Y 50/00; B33Y 50/02
See application file for complete search history.

(56) References Cited

U.S. PATENT DOCUMENTS

| 4,155,969 | A | * | 5/1979 | Hendry | B29C 44/421 |
| | | | | | 264/DIG. 83 |
| 5,980,098 | A | * | 11/1999 | Meier-Kaiser | B29B 7/603 |
| | | | | | 366/76.3 |
| 12,070,896 | B2 | * | 8/2024 | Piccirelli | B29C 64/314 |
| 2004/0159964 | A1 | * | 8/2004 | Lavoie | H01M 4/0411 |
| | | | | | 264/408 |

(Continued)

FOREIGN PATENT DOCUMENTS

CN 109130136 A * 1/2019 ......... B29C 45/2708

*Primary Examiner* — Nahida Sultana

(57) ABSTRACT

Recently, we have introduced 3D-micro-patterned pharmaceutical dosage forms for enhancing the efficacy, safety, convenience, and cost-effectiveness of drug therapies. Presented herein are an apparatus and a method for the manufacture of such dosage forms. The apparatus comprises at least a first extruder and at least a second extruder. The first extruder comprises an extruder channel having an exit port with a valve mated to an input port of a second extruder. Said second extruder comprises a translatable piston for extruding plasticized fiber at controlled speed. The apparatus further comprises a stage movable at the controlled speed of the extruded fiber for depositing said fiber to a three dimensional structural framework. The method includes extruding plasticized matrix from a first extruder into a second extruder, extruding said plasticized matrix from the second extruder through a fiber fabrication exit port at controlled speed to form extruded fiber, and depositing said extruded fiber onto a fiber assembling stage to form a three dimensional structural framework.

23 Claims, 20 Drawing Sheets

(56) References Cited

U.S. PATENT DOCUMENTS

| | | | | |
|---|---|---|---|---|
| 2007/0087100 | A1* | 4/2007 | Fornaguera | A23G 3/54 |
| | | | | 426/516 |
| 2015/0099025 | A1* | 4/2015 | Spalt | B33Y 50/02 |
| | | | | 425/166 |
| 2015/0306823 | A1* | 10/2015 | Askedall | B29C 64/236 |
| | | | | 425/131.1 |
| 2019/0133956 | A1* | 5/2019 | Haupts | A61K 31/135 |
| 2020/0086564 | A1* | 3/2020 | Lewis | B33Y 10/00 |
| 2020/0391416 | A1* | 12/2020 | Burnham | B29C 44/32 |
| 2021/0008779 | A1* | 1/2021 | Ding Yi | B29C 48/0012 |
| 2021/0291443 | A1* | 9/2021 | Bai | B29C 64/209 |
| 2023/0139210 | A1* | 5/2023 | Saurwalt | B33Y 50/02 |
| | | | | 425/162 |
| 2023/0311417 | A1* | 10/2023 | Vanerio | B29C 64/209 |
| | | | | 425/61 |
| 2023/0321905 | A1* | 10/2023 | Cha | B29C 64/209 |
| | | | | 425/143 |
| 2024/0181703 | A1* | 6/2024 | Reinhardt | B29C 64/106 |

* cited by examiner

METHOD FOR 3D-MICRO-PATTERNING

CROSS-REFERENCE TO RELATED APPLICATIONS

This application is a continuation of, and incorporates herein by reference in its entirety, the International Application No. PCT/US2021/022860 filed on Mar. 17, 2021 and titled "Method and apparatus for 3D-micro-patterning", which claims priority to and the benefit of the U.S. Provisional Application No. 62/991,052 filed on Mar. 17, 2020, the U.S. Provisional Application No. 63/085,893 filed on Sep. 30, 2020, and the U.S. Provisional Application No. 63/158,870 filed on Mar. 9, 2021. All foregoing applications are hereby incorporated by reference in their entirety.

This application is related to, and incorporates herein by reference in their entirety, the U.S. application Ser. No. 15/482,776 filed on Apr. 9, 2017 and titled "Fibrous dosage form", the U.S. application Ser. No. 15/964,058 filed on Apr. 26, 2018 and titled "Method and apparatus for the manufacture of fibrous dosage forms", the U.S. application Ser. No. 16/860,911 filed on Apr. 28, 2020 and titled "Expandable structured dosage form for immediate drug delivery", the U.S. application Ser. No. 16/916,208 filed on Jun. 30, 2020 and titled "Dosage form comprising structural framework of two-dimensional elements", the International Application No. PCT/US19/19004 filed on Feb. 21, 2019 and titled "Expanding structured dosage form", and the International Application No. PCT/US19/52030 filed on Sep. 19, 2019 and titled "Dosage form comprising structured solid-solution framework of sparingly-soluble drug and method for manufacture thereof".

FIELD OF THE INVENTION

This invention relates generally to methods and apparatuses for the manufacture of fibrous solids, and more particularly to methods and apparatuses for the manufacture of fibrous dosage forms. In some embodiments, the invention herein relates to a method and apparatus for the manufacture of fibrous dosage forms with predictable microstructure.

BACKGROUND OF THE INVENTION

Recently, the present inventors (Blaesi and Saka) have introduced 3D-micro-patterned pharmaceutical dosage forms for enhancing the efficacy, safety, convenience, and cost-effectiveness of drug therapies. A manufacturing process comprising extruding a plasticized matrix through an exit port of an extrusion channel to form a plasticized fiber, and structuring said plasticized fiber to a three dimensional structural network by depositing it on a translating stage was also presented. For further details related to prior work, see, e.g., the U.S. application Ser. No. 15/964,058 filed on Apr. 26, 2018 and titled "Method and apparatus for the manufacture of fibrous dosage forms".

In order to produce dosage forms with precisely controlled microstructure by this extrusion-deposition process, the velocity of the extruded fiber and the velocity of the moving stage should be the same. The velocity of the moving stage can generally be very precisely controlled by actuation with electric servo or stepper motors. The velocity of the extruded fiber, however, is more difficult to control. If it is too variable, microstructural control of the deposited dosage form structure is compromised.

In this disclosure, therefore, an apparatus and a method are disclosed for 3D-micro-patterning fibrous dosage forms with precisely controlled microstructure. The disclosed apparatus and method enable faster and more economical manufacture of dosage forms with a greater range of properties, more precisely controlled properties, and so on.

SUMMARY OF THE INVENTION

Generally, an apparatus as disclosed herein comprises at least a first extruder and at least a second extruder. The first extruder comprises an extruder channel having an exit port with a valve mated to an input port of a second extruder. Said second extruder comprises a translatable piston for extruding plasticized fiber at controlled speed. The apparatus further comprises a stage movable at the controlled speed of the extruded fiber for depositing said fiber to a three dimensional structural framework. The method includes extruding plasticized matrix from a first extruder into a second extruder, extruding said plasticized matrix from the second extruder through a fiber fabrication exit port at controlled speed to form extruded fiber, and depositing said extruded fiber onto a fiber assembling stage to form a three dimensional structural framework.

More specifically, in one aspect, this invention comprises an apparatus for manufacturing pharmaceutical solid dosage forms. Said apparatus comprising at least one first extruder and at least one second extruder. Said first extruder comprising an extrusion channel with feeding ports for injecting drug, excipient, and solvent into the extrusion channel Said first extruder further comprising means for forming and extruding a plasticized matrix in said first extruder extrusion channel Said first extruder extrusion channel terminating at at least one exit port, said at least one exit port having at least a valve, said valve mated to at least one input port of at least one second extruder. Said second extruder comprising its own extrusion channel defined by channel walls, the channel having a closed first end and a second exit port end. Said channel walls in contact with and enclosing a piston translatable along the channel's longitudinal axis between said first and second ends, wherein said piston recedes towards said first end upon filling of the extrusion channel with plasticized matrix from the first extruder. Said second extruder further comprising means for translating the piston and thereby conveying the plasticized matrix at a controlled speed towards the second end, said second end terminating in a fiber fabrication exit port for extruding the conveyed plasticized matrix and manufacturing the dosage forms. Said apparatus further comprising a translating or rotating stage movable in the x, y, and z directions at the controlled speed of the exiting, extruded plasticized fiber, whereby the exiting fiber can be assembled into a three dimensional structural framework by depositing said fiber along a path defined by motion of said stage.

In another aspect, this invention comprises an apparatus for manufacturing pharmaceutical solid dosage forms, said apparatus comprising at least one first extruder and at least one second extruder. Said first extruder comprising an extrusion channel with feeding ports for injecting drug and excipient into the extrusion channel Said first extruder further comprising at least a heating element, and means for forming and extruding a plasticized matrix in said first extruder extrusion channel Said first extruder extrusion channel terminating at at least one exit port, said at least one exit port having at least a valve, said valve mated to at least one input port of at least one second extruder. Said second extruder comprising its own extrusion channel defined by channel walls, the channel having a closed first end and a second exit port end. Said channel walls in contact with and enclosing a piston translatable along the channel's longitudinal axis between said first and second ends, wherein said piston recedes towards said first end upon filling of the extrusion channel with plasticized matrix from the first extruder. Said second extruder further comprising means for translating the piston and thereby conveying the plasticized matrix at a controlled speed towards the second end, said second end terminating in a fiber fabrication exit port for extruding the conveyed plasticized matrix and manufacturing the dosage forms. Said apparatus further comprising a translating or rotating stage movable in the x, y, and z directions at the controlled speed of the exiting, extruded plasticized fiber, whereby the exiting fiber can be assembled into a three dimensional structural framework by depositing said fiber along a path defined by motion of said stage.

In another aspect, the invention herein comprises an apparatus for manufacturing pharmaceutical solid dosage forms, said apparatus comprising at least one first extruder and at least one second extruder. Said first extruder comprising an extrusion channel with feeding ports for injecting drug, excipient, and solvent into the extrusion channel Said first extruder further comprising means for forming and extruding a plasticized matrix in said first extruder extrusion channel Said first extruder extrusion channel terminating at at least one exit port, said at least one exit port having a check valve, and said exit port mated to at least one input port of at least one second extruder. Said second extruder comprising its own extrusion channel defined by channel walls, the channel having a closed first end and a second exit port end. Said channel walls in contact with and enclosing a piston translatable along the channel's longitudinal axis between said first and second ends, wherein said piston recedes towards said first end upon filling of the extrusion channel with plasticized matrix from the first extruder. Said second extruder further comprising means for translating the piston and thereby conveying the plasticized matrix at a controlled speed towards the second end, said second end terminating in a fiber fabrication exit port for extruding the conveyed plasticized matrix and manufacturing the dosage forms. Said apparatus further comprising a movable solid surface removably attached to the fiber fabrication exit port to flexibly block flow of plasticized matrix through the fiber fabrication exit port. Said apparatus further comprising a translating or rotating stage movable in the x, y, and z directions at the controlled speed of the exiting, extruded plasticized fiber, whereby the exiting fiber can be assembled into a three dimensional structural framework by depositing said fiber along a path defined by motion of said stage; and the movable solid surface is attached to or included in the movable stage.

In another aspect, the invention herein comprises an apparatus for manufacturing pharmaceutical solid dosage forms comprising at least one first extruder and at least one second extruder. Said first extruder comprising an extrusion channel with feeding ports for injecting drug, excipient, and solvent into the extrusion channel and one or more rotatable screws for forming and extruding a plasticized matrix therein. Said first extruder extrusion channel terminating at at least one exit port, said at least one exit port having a check valve, and said exit port mated to at least one input port of at least one second extruder. Said second extruder comprising its own extrusion channel defined by channel walls, the channel having a closed first end and a second exit port end. Said channel walls in contact with and enclosing a piston translatable along the channel's longitudinal axis between said first and second ends, wherein said piston recedes towards said first end upon filling of the extrusion channel with plasticized matrix from the first extruder. Said second extruder further comprising an electric motor for translating the piston and thereby conveying the plasticized matrix at a controlled speed towards the second end, said second end terminating in a fiber fabrication exit port for extruding the conveyed plasticized matrix and manufacturing the dosage forms. Said apparatus further comprising a movable solid surface removably attached to the fiber fabrication exit port to flexibly block flow of plasticized matrix through the fiber fabrication exit port. Said apparatus further comprising a translating or rotating stage movable in the x, y, and z directions at the controlled speed of the exiting, extruded plasticized fiber, whereby the exiting fiber can be assembled into a three dimensional structural framework by depositing said fiber along a path defined by motion of said stage; and the movable solid surface is attached to or included in the movable stage.

In some embodiments, a valve allows flow of plasticized matrix from a first extruder extrusion channel through an exit port of said first extruder extrusion channel and into the channel of a second extruder while a piston of said second extruder recedes and said second extruder extrusion channel is filled with plasticized matrix.

In some embodiments, a valve blocks flow of plasticized matrix from the channel of a second extruder through a first extruder's exit port while a piston of said second extruder advances to extrude fiber through a fiber fabrication exit port.

In some embodiments, at least one valve comprises a check valve permitting flow of plasticized matrix from said first extruder channel into said second extruder channel, and blocking flow from said second extruder channel into said first extruder channel.

In some embodiments, at least one valve comprises a check valve, and wherein said check valve has a cracking pressure in the range between 0.01 MPa and 1000 MPa (e.g., between 0.05 MPa and 500 MPa, or between 0.1 MPa and 500 MPa).

In some embodiments, at least one valve comprises a passive valve.

In some embodiments, an apparatus further comprises a movable solid surface removably attached to a fiber fabrication exit port to flexibly block flow of plasticized matrix through said fiber fabrication exit port.

In some embodiments, an apparatus further comprises a movable solid surface removably attached to a fiber fabrication exit port to flexibly block flow of plasticized matrix through said fiber fabrication exit port, and wherein the composition of a movable solid surface comprises an elastic modulus smaller than the elastic modulus of the channel wall defining said fiber fabrication exit port.

In some embodiments, the composition of a movable solid surface comprises a fluoropolymer.

In some embodiments, a movable solid surface is included in or attached to a translating or rotating stage.

In some embodiments, a valve comprises a three-way valve. In some embodiments, a valve comprises a three-way valve, and wherein said three-way valve comprises a flow path permitting flow of plasticized matrix from said first extruder channel into said second extruder channel while blocking flow of plasticized matrix from said first extruder channel towards a fiber fabrication exit port of said second extruder extrusion channel.

In some embodiments, a valve comprises a three-way valve, and wherein said three-way valve comprises a flow path allowing flow through a second extruder extrusion channel and through a fiber fabrication exit port of said second extruder extrusion channel, while blocking flow from said second extruder extrusion channel into an extrusion channel of a first extruder.

In some embodiments, a valve comprises a three-way valve, and wherein said three-way valve is operated by an actuator to switch from one flow path to another flow path.

In some embodiments, an apparatus further comprises a second valve, said second valve positioned between an input port of the second extruder extrusion channel and a fiber fabrication exit port to flexibly block flow of plasticized matrix through said fiber fabrication exit port.

In some embodiments, means for forming and extruding a plasticized matrix in the first extruder extrusion channel comprises one or more rotatable screws.

In some embodiments, means for forming and extruding a plasticized matrix in the first extruder extrusion channel comprises one or more rotatable screws, and wherein said one or more rotatable screws are driven by at least an electric motor.

In some embodiments, a cross sectional area of a second extruder extrusion channel enclosing a piston is in the range between 0.001 cm$^2$ and 50 cm$^2$.

In some embodiments, a cross sectional area of a second extruder extrusion channel enclosing a piston is no greater than 10 cm$^2$.

In some embodiments, a cross sectional area of the second extruder extrusion channel tapers down or contracts before a fiber fabrication exit port to the cross sectional area of said exit port.

In some embodiments, a cross sectional area of the second extruder extrusion channel tapers down before a fiber fabrication exit port, and wherein the angle of said taper is no greater than 60 degrees (e.g., no greater than 45 degrees, or no greater than 35 degrees).

In some embodiments, a second extruder extrusion channel comprises no more than ten fiber fabrication exit ports.

In some embodiments, a second extruder extrusion channel comprises no more than one fiber fabrication exit port.

In some embodiments, means for translating said piston comprises an electric motor.

In some embodiments, said piston comprises a seal around its circumference to block flow of plasticized matrix through the first end of said second extruder extrusion channel.

In some embodiments, said piston comprises a seal around its circumference to block flow of plasticized matrix through the first end of said second extruder extrusion channel, and wherein the seal comprises an elastic modulus smaller than the elastic modulus of the second extruder extrusion channel wall.

In some embodiments, said piston comprises a seal around its circumference to block flow of plasticized matrix through the first end of said second extruder extrusion channel, and wherein the composition of the seal comprises a fluoropolymer.

In some embodiments, said fiber fabrication exit port is designed to extrude fibrous extrudate with a fiber thickness no greater than 2.5 mm.

In some embodiments, said fiber fabrication exit port is designed to extrude fibrous extrudate with a fiber thickness in the range between 10 μm and 2.5 mm.

In some embodiments, the first extruder extrusion channel bifurcates into multiple exit ports having a valve, and wherein at least two valves are mated to input ports of at least two second extruders.

In some embodiments, the first extruder extrusion channel bifurcates into multiple exit ports having a valve, wherein at least two valves are mated to input ports of at least two second extruders, and wherein each second extruder comprises a translatable piston.

In some embodiments, the first extruder extrusion channel bifurcates into multiple exit ports having a valve, wherein at least two valves are mated to input ports of at least two second extruders, and wherein each second extruder comprises a translatable piston, and wherein at least two pistons of at least two second extruders are translatable by a single electric motor.

In another aspect, the invention herein comprises a method of manufacturing pharmaceutical solid dosage forms comprising the steps of: injecting at least one of each active ingredient, excipient, and solvent into the extrusion channel of at least one first extruder, said channel terminating at at least one exit port, said at least one exit port having at least a valve, said valve mated to at least one input port of at least one second extruder; mixing the active ingredient, excipient, and solvent to form a plasticized matrix; conveying said plasticized matrix to said first extruder's exit port; extruding the conveyed plasticized matrix through said exit port and valve, thereby filling at least one extrusion channel of at least one second extruder with said extruded plasticized matrix, said second extruder channel terminating at at least one fiber fabrication exit port; extruding the plasticized matrix in said second extruder extrusion channel through said fiber fabrication port at a controlled speed; and depositing the extruded plasticized fiber onto a fiber assembling stage to a form a three dimensional fiber structural framework defined by the motion of said stage at the speed of the exiting extruded, plasticized fiber.

In another aspect, the invention herein comprises a method of manufacturing pharmaceutical solid dosage forms comprising the steps of injecting at least one of each active ingredient and excipient into the extrusion channel of at least one first extruder, said channel terminating at at least one exit port, said at least one exit port having at least a valve, said valve mated to at least one input port of at least one second extruder; mixing and heating the active ingredient and excipient to form a plasticized matrix; conveying said plasticized matrix to said first extruder's exit port; extruding the conveyed plasticized matrix through said exit port and valve, thereby filling at least one extrusion channel of at least one second extruder with said extruded plasticized matrix, said second extruder channel terminating at at least one fiber fabrication exit port; extruding the plasticized matrix in said second extruder extrusion channel through said fiber fabrication port at a controlled speed; and depositing the extruded plasticized fiber onto a fiber assembling stage to a form a three dimensional fiber structural framework defined by the motion of said stage at the speed of the exiting extruded, plasticized fiber.

In another aspect, the invention herein comprises a method of manufacturing pharmaceutical solid dosage forms comprising the steps of injecting at least one of each active ingredient, excipient, and solvent into the extrusion channel of at least one first extruder, said channel terminating at at least one exit port, said at least one exit port having at least a check valve, and said exit port mated to at least one input port of at least one second extruder; mixing the active ingredient, excipient, and solvent to form a plasticized matrix; conveying said plasticized matrix to said first extruder's exit port; extruding the conveyed plasticized matrix through said exit port, thereby filling at least one extrusion channel of at least one second extruder with said extruded plasticized matrix, said second extruder channel terminating at at least one fiber fabrication exit port; attaching a movable solid surface to the fiber fabrication exit port while plasticized matrix is extruded through the check valve into the channel of the second extruder to prevent or block flow of plasticized matrix through said fiber fabrication exit port; moving a movable solid surface away from the fiber fabrication exit port to allow flow of plasticized matrix through said fiber fabrication exit port; extruding the plasticized matrix in said second extruder extrusion channel through said fiber fabrication port at a controlled speed; and depositing the extruded plasticized fiber onto a fiber assembling stage to a form a three dimensional fiber structural framework defined by the motion of said stage at the speed of the exiting extruded, plasticized fiber.

In another aspect, the invention herein comprises a method of manufacturing pharmaceutical solid dosage forms comprising the steps of injecting at least one of each active ingredient, excipient, and solvent into the extrusion channel of at least one first extruder, said channel terminating at at least one exit port, said at least one exit port having at least a check valve, and said exit port mated to at least one input port of at least one second extruder; mixing the injected active ingredient, excipient, and solvent to form a plasticized matrix; conveying said plasticized matrix to said first extruder's exit port; extruding the conveyed plasticized matrix through said exit port, thereby filling at least one extrusion channel of at least one second extruder with said extruded plasticized matrix, said second extruder channel terminating at at least one fiber fabrication exit port; attaching a movable solid surface to the fiber fabrication exit port while plasticized matrix is extruded through the check valve into the channel of the second extruder to prevent or block flow of plasticized matrix through said fiber fabrication exit port; moving a movable solid surface away from the fiber fabrication exit port to allow flow of plasticized matrix through said fiber fabrication exit port; extruding the plasticized matrix in said second extruder extrusion channel through said fiber fabrication port at a controlled speed using an advancing piston driven by an electric motor; and depositing the extruded plasticized fiber onto a fiber assembling stage to a form a three dimensional fiber structural framework defined by the motion of said stage at the speed of the exiting extruded, plasticized fiber; wherein the movable solid surface is attached to or included in the fiber assembling stage.

In some embodiments, a valve allows flow of plasticized matrix from a first extruder extrusion channel through an exit port of said first extruder extrusion channel and into the channel of a second extruder while a piston of said second extruder recedes and said second extruder extrusion channel is filled with plasticized matrix.

In some embodiments, a valve blocks flow of plasticized matrix from the channel of a second extruder through a first extruder's exit port while a piston of said second extruder advances to extrude fiber through a fiber fabrication exit port.

In some embodiments, a valve comprises a check valve permitting flow of plasticized matrix from said first extruder channel into said second extruder channel, and blocking flow from said second extruder channel into said first extruder channel.

In some embodiments, a check valve has a cracking pressure in the range between 0.01 MPa and 1000 MPa (e.g., between 0.05 MPa and 500 MPa, or between 0.1 MPa and 500 MPa).

In some embodiments, the valve comprises a passive valve.

In some embodiments, a method further comprises removably attaching a movable solid surface to a fiber fabrication exit port to flexibly block flow of plasticized matrix through said fiber fabrication exit port.

In some embodiments, a method further comprises moving a movable solid surface away from a fiber fabrication exit port to allow flow of plasticized matrix through said fiber fabrication exit port.

In some embodiments, a method further comprises a movable solid surface removably attached to a fiber fabrication exit port to flexibly block flow of plasticized matrix through said fiber fabrication exit port.

In some embodiments, a method further comprises a movable solid surface removably attached to a fiber fabrication exit port to flexibly block flow of plasticized matrix through said fiber fabrication exit port, wherein the composition of the movable solid surface comprises an elastic modulus smaller than the elastic modulus of the channel wall defining said fiber fabrication exit port.

In some embodiments, a composition of a movable solid surface comprises a fluoropolymer.

In some embodiments, a movable solid surface is included in or attached to a fiber assembling stage.

In some embodiments, a valve comprises a three-way valve.

In some embodiments, the valve comprises a three-way valve, and wherein said three-way valve comprises a flow path permitting flow of plasticized matrix from said first extruder channel into said second extruder channel while blocking flow of plasticized matrix from said first extruder channel towards a fiber fabrication exit port of said second extruder extrusion channel.

In some embodiments, a valve comprises a three-way valve, and wherein said three-way valve comprises a flow path allowing flow through a second extruder extrusion channel and through a fiber fabrication exit port of said second extruder extrusion channel, while blocking flow from said second extruder extrusion channel into an extrusion channel of a first extruder.

In some embodiments, at least one valve comprises a three-way valve, and wherein said three-way valve is operated by an actuator to switch from one flow path to another flow path.

In some embodiments, a method further comprises the use of a second valve to flexibly block flow of plasticized matrix through a fiber fabrication exit port of a second extruder extrusion channel, said second valve positioned between an input port and a fiber fabrication exit port of said second extruder extrusion channel.

In some embodiments, a second valve blocks flow of plasticized matrix from a first extruder extrusion channel to an exit port of a second extruder extrusion channel while said second extruder extrusion channel is filled with plasticized matrix.

In some embodiments, the method further comprises flexibly blocking flow of plasticized matrix through a fiber fabrication exit port using a second valve, and wherein said second valve allows flow of plasticized matrix through a channel of a second extruder and through a fiber fabrication exit port of said second extruder extrusion channel while fiber is extruded through said fiber fabrication exit port.

In some embodiments, one or more rotatable screws are used for forming and extruding plasticized matrix in the first extruder extrusion channel.

In some embodiments, one or more rotatable screws are driven by at least an electric motor.

In some embodiments, plasticized matrix in a second extruder extrusion channel is extruded through a fiber fabrication port of said second extruder extrusion channel at a controlled speed using an advancing piston in contact with and enclosed by said second extruder extrusion channel.

In some embodiments, plasticized matrix in a second extruder extrusion channel is extruded through a fiber fabrication port of said second extruder extrusion channel at a controlled speed using an advancing piston driven by an electric motor.

In some embodiments, a cross sectional area of a second extruder extrusion channel is in the range between 0.001 $cm^2$ and 50 $cm^2$.

In some embodiments, a cross sectional area of a second extruder extrusion channel is no greater than 10 $cm^2$.

In some embodiments, the cross sectional area of the second extruder extrusion channel tapers down or contracts before a fiber fabrication exit port to the cross sectional area of said exit port.

In some embodiments, the cross sectional area of the second extruder extrusion channel tapers down before a fiber fabrication exit port, and wherein the angle of said taper is no greater than 60 degrees (e.g., no greater than 45 degrees, or no greater than 35 degrees).

In some embodiments, a second extruder extrusion channel comprises no more than ten fiber fabrication exit ports.

In some embodiments, a second extruder extrusion channel comprises no more than one fiber fabrication exit port.

In some embodiments, plasticized matrix in a second extruder extrusion channel is extruded through a fiber fabrication port of said second extruder extrusion channel at a controlled speed using an advancing piston in contact with and enclosed by said second extruder extrusion channel, and wherein said piston comprises a seal around its circumference to block or restrict flow of plasticized matrix through the first end of said second extruder extrusion channel.

In some embodiments, plasticized matrix in a second extruder extrusion channel is extruded through a fiber fabrication port of said second extruder extrusion channel at a controlled speed using an advancing piston in contact with and enclosed by said second extruder extrusion channel, and wherein said piston comprises a seal around its circumference to block flow of plasticized matrix through the first end of said second extruder extrusion channel, and wherein the seal comprises an elastic modulus smaller than the elastic modulus of the second extruder extrusion channel wall.

In some embodiments, plasticized matrix in a second extruder extrusion channel is extruded through a fiber fabrication port of said second extruder extrusion channel at a controlled speed using an advancing piston in contact with and enclosed by said second extruder extrusion channel, and wherein said piston comprises a seal around its circumference to block flow of plasticized matrix through the first end of said second extruder extrusion channel, and wherein the composition of said seal comprises a fluoropolymer.

In some embodiments, a fiber fabrication exit port is designed to extrude fibrous extrudate with a fiber thickness no greater than 2 mm.

In some embodiments, the first extruder extrusion channel bifurcates into multiple exit ports having a valve, and wherein at least two valves are mated to input ports of at least two second extruders.

In some embodiments, the first extruder extrusion channel bifurcates into multiple exit ports having a valve, wherein at least two valves are mated to input ports of at least two second extruders, and wherein each second extruder comprises a translatable piston.

In some embodiments, the first extruder extrusion channel bifurcates into multiple exit ports having a valve, wherein at least two valves are mated to input ports of at least two second extruders, and wherein each second extruder comprises a translatable piston, and wherein at least two pistons of at least two second extruders are translatable by a single electric motor.

In some embodiments, the viscosity of an extruded, exiting plasticized fiber is in the range between 10 Pa·s and 100,000 Pa·s (e.g., 50 Pa·s-50,000 Pa·s, 75 Pa·s-25,000 Pa·s) at a shear rate of 1/s.

In another aspect, this invention comprises an apparatus for manufacturing pharmaceutical solid dosage forms comprising at least one first extruder and at least one second extruder. Said first extruder comprising an extrusion channel with feeding ports for injecting drug, excipient, and solvent into the extrusion channel, and means for forming and extruding a plasticized matrix therein. Said first extruder extrusion channel terminating at at least one exit port, said at least one exit port having a first valve, said first valve mated to at least one input port of at least one second extruder. Said second extruder comprising its own extrusion channel defined by channel walls, the channel having a closed first end, a second exit port end, and a second valve between said input port and said second end. Said channel walls in contact with and enclosing a piston translatable along the channel's longitudinal axis between said first and second ends, wherein said piston recedes towards said first end upon filling of the extrusion channel with plasticized matrix from the first extruder. Said second extruder further comprising means for translating the piston and thereby conveying the plasticized matrix at a controlled speed towards the second end, said second end terminating in a fiber fabrication exit port for extruding the conveyed plasticized matrix and manufacturing the dosage forms. Said apparatus or second extruder further comprising a translating or rotating stage movable in the xy, and z directions at the controlled speed of the exiting, extruded plasticized fiber; whereby the exiting fiber can be assembled into a three dimensional structural framework by depositing said fiber along a path defined by motion of said stage.

In another aspect, the invention herein comprises a method of manufacturing pharmaceutical solid dosage forms comprising the steps of injecting at least one of each active ingredient, excipient, and solvent into the extrusion channel of at least one first extruder, said channel terminating at at least one exit port, said at least one exit port having at least a first valve, said first valve mated to at least one input port of at least one second extruder; mixing the active ingredient, excipient, and solvent to form a plasticized matrix; conveying said plasticized matrix to said first extruder's at least one exit port; extruding the conveyed plasticized matrix through said exit port and first valve, thereby filling at least one extrusion channel of at least one second extruder with said extruded plasticized matrix, said second extruder channel terminating at at least one fiber fabrication exit port, and having at least a second valve between an input port and a fiber fabrication exit port of said second extruder; extruding the plasticized matrix in said second extruder extrusion channel through said second valve and said fiber fabrication port at a controlled speed using an advancing piston; and depositing the extruded plasticized fiber onto a fiber assembling stage to a form a three dimensional fiber structural framework defined by the motion of said stage at the speed of the exiting, extruded plasticized fiber.

In some embodiments, a first valve allows flow of plasticized matrix from a first extruder extrusion channel through an exit port of said first extruder extrusion channel and into the channel of a second extruder while a piston of said second extruder recedes and said second extruder extrusion channel is filled with plasticized matrix.

In some embodiments, a first valve blocks flow of plasticized matrix from the channel of a second extruder through a first extruder's exit port while a piston of said second extruder advances to extrude fiber through a fiber fabrication exit port.

In some embodiments, a second valve blocks flow of plasticized matrix from a first extruder extrusion channel to a fiber fabrication exit port of a second extruder extrusion channel while a piston of said second extruder recedes and said second extruder extrusion channel is filled with plasticized matrix.

In some embodiments, a second valve allows flow of plasticized matrix through a channel of a second extruder and through a fiber fabrication exit port of said second extruder extrusion channel while a piston of said second extruder advances to extrude fiber through a fiber fabrication exit port.

Additional elements of the method and apparatus disclosed herein are described throughout this specification. Elements of embodiments described with respect to one aspect of the invention can be applied with respect to another aspect. By way of example but not by way of limitation, certain embodiments of the method claims can include features of the apparatus claims, and vice versa.

This invention may be better understood by reference to the accompanying drawings, attention being called to the fact that the drawings are primarily for illustration, and should not be regarded as limiting.

BRIEF DESCRIPTION OF THE DRAWINGS

The objects, embodiments, features, and advantages of the present invention are more fully understood when considered in conjunction with the following accompanying drawings.

DEFINITIONS

Figure 1:
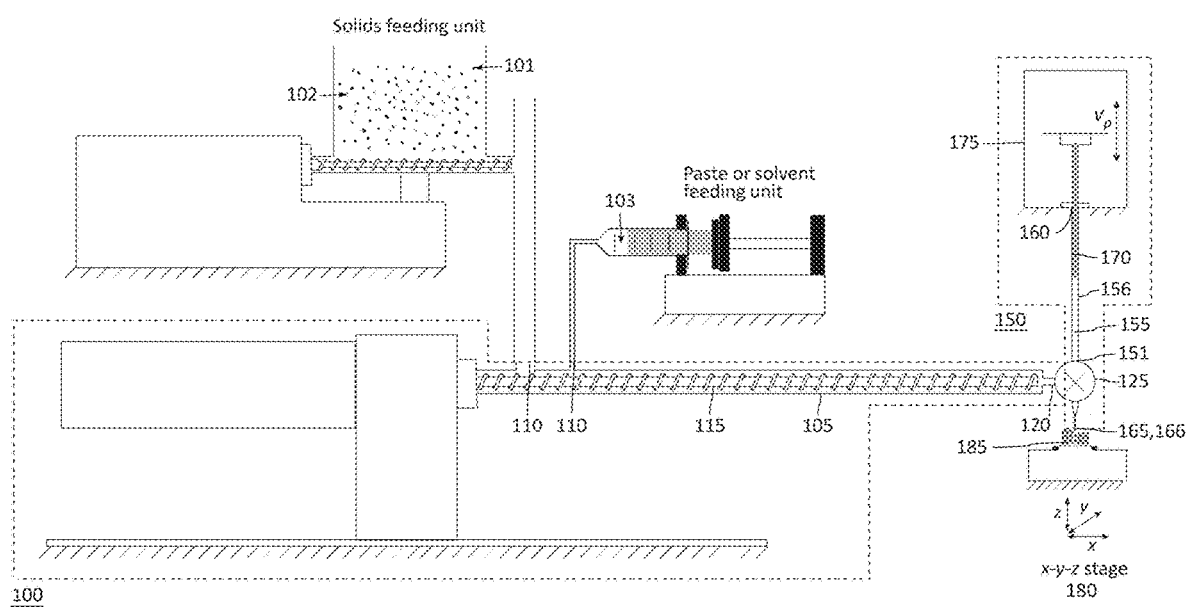
FIG. 1 presents a non-limiting schematic of an apparatus and a method according to this invention.

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises" are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

Moreover, in the disclosure herein, the terms "one or more active ingredients", "active ingredient", "active pharmaceutical ingredient", and "drug" are used interchangeably. As used herein, an "active ingredient" or "active agent" refers to an agent whose presence or level correlates with elevated level or activity of a target, as compared with that observed absent the agent (or with the agent at a different level). In some embodiments, an active ingredient is one whose presence or level correlates with a target level or activity that is comparable to or greater than a particular reference level or activity (e.g., that observed under appropriate reference conditions, such as presence of a known active agent, e.g., a positive control).

A granular solid in this disclosure generally comprises a conglomeration, collection, accumulation, etc. of discrete solid particles of a specific composition. The average size of the particulates (e.g., the average diameter or the third root of the average volume) may be in the range from about 0.001 µm or smaller to about 150 mm or greater. This includes, but is not limited to an average size of the particulates of 0.002 µm-200 mm, 0.005 µm-200 mm, 0.01 µm-150 mm, 0.05 µm-150 mm, 0.1 µm-150 mm; 1 µm-100 mm, 1 µm-50 mm, 5 µm-50 mm, 10 µm-50 mm, or 5 µm-30 mm. Typically, however, pharmaceutical granular solids have an average particle size in the range of about 0.1 µm to 1 mm.

In the invention herein, a "solid" or "solid material" is typically referred to an elastic or viscoelastic material. Such elastic or viscoelastic materials may be characterized by a very large viscosity that may be far greater than about $10^5$ Pa·s. This includes, but is not limited to a viscosity greater than $10^7$ Pa·s, or greater than $10^{10}$ Pa·s. In the limiting case, the viscosity is so large that it is difficult to measure. A solid material may be considered "fully elastic" or "elastic" in this case. For further details about the mechanical behavior of elastic or visco-elastic materials, see, e.g., K. L. Johnson, "Contact mechanics", Cambridge University Press, 1985.

In the context of the invention herein, a plasticized matrix generally is a viscous material comprising a shear viscosity in the range of 0.01 Pa·s-5×$10^8$ Pa·s at a shear rate no greater than 10 l/s. This includes but is not limited to a minimum shear viscosity of 0.01 Pa·s-$10^8$, 0.01 Pa·s-5×$10^7$ Pa·s, 0.025 Pa·s-10,000,000 Pa·s, 0.05 Pa·s-5,000,000 Pa·s, 0.1 Pa·s-2,000,000 Pa·s, 0.25 Pa·s-1,000,000 Pa·s, 0.25 Pa·s-5,000,000 Pa·s, 0.5 Pa·s-2,000,000 Pa·s, 1 Pa·s-2,000,000 Pa·s, 1 Pa·s-5,000,000 Pa·s, 1 Pa·s-1,000,000 Pa·s, 10 Pa·s-1,000,000 Pa·s, 50 Pa·s-1,000,000 Pa·s, 100 Pa·s-1,000,000 Pa·s, or 1 Pa·s-500,000 Pa·s at a shear rate no greater than 10 l/s. Non-limiting examples of plasticized matrices include but are not limited to polymer melts, concentrated solutions of one or more polymers and one or more solvents (e.g., water, ethanol, acetone, isopropanol, ethyl acetate, dimethyl sulfoxide, etc.), suspensions of solid particulates or granules and a polymer melt, or suspensions of solid particulates and a concentrated polymeric solution, etc. It may be noted that in the context of the invention herein the terms "plasticized matrix", "plasticized matrices", "plasticized material", and "melt" are used interchangeably. Furthermore, in some embodiments a plasticized matrix may include an active ingredient. The active ingredient may be molecularly dissolved in the plasticized matrix, dispersed as particles in the plasticized matrix, etc.

Furthermore, in some embodiments of the invention herein, a three dimensional structural network or framework of drug-containing fibers generally comprises a drug-containing fibrous structure (e.g., an assembly or an assemblage of one or more fibers) that extends over a length, width, and thickness greater than 200 µm. This includes, but is not limited to drug-containing fibrous structures that extend over a length, width, and thickness greater than 300 µm, or greater than 500 µm, or greater than 700 µm, or greater than 1 mm, or greater than 1.25 mm, or greater than 1.5 mm, or greater than 2 mm.

Similarly, in some embodiments, a three dimensional structural network or framework of drug-containing fibers may comprise a drug-containing fibrous structure (e.g., an assembly or an assemblage of one or more fibers) that extends over a length, width, and thickness greater than the average thickness of at least one fiber (or at least one fiber segment) in the three dimensional structural network of fibers. This includes, but is not limited to drug-containing fibrous structures that extend over a length, width, and thickness greater than 1.5, or greater than 2, or greater than 2.5, or greater than 3, or greater than 3.5, or greater than 4 times the average thickness of at least one fiber (or at least one fiber segment) in the three dimensional structural network of fibers. It may be noted that the terms "three dimensional structural network of drug-containing fibers", "three dimensional structural network of fibers", "three dimensional structural network of one or more fibers", "three dimensional structural network of one or more drug-containing fibers", "three dimensional network of fibers", "framework", and "framework of fibers" are used interchangeably herein.

Moreover, as used herein, the terms "fiber", "fibers", "one or more fibers", "one or more drug-containing fibers", and "drug-containing fibers", are used interchangeably. They are understood as the drug-containing structural elements (or building blocks) that make up a three dimensional structural network of drug-containing fibers. Fibers can be either solid or plasticized. The terms "plasticized fiber" and "wet fiber" are used interchangeably herein. Plasticized and wet fibers are understood as viscous fibers with a viscosity of the order of the viscosity of the plasticized matrix from which they were formed.

A fiber has a length much greater than its width and thickness (e.g., the length of a fiber is much greater than its width and the length of a fiber is much greater than its thickness). In the present disclosure, a fiber is referred to as having a length greater than 2 times its width and thickness. This includes, but is not limited to a fiber length greater than 3 times, or greater than 4 times, or greater than 5 times, or greater than 6 times, or greater than 8 times, or greater than 10 times, or greater than 12 times the fiber width and thickness. In yet other embodiments that are included but not limiting in the disclosure herein, the length of a fiber may be greater than 0.3 mm, or greater than 0.5 mm, or greater than 1 mm, or greater than 2.5 mm.

Moreover, as used herein, the term "fiber segment" refers to a fraction of a fiber along the length of said fiber.

In the invention disclosed herein, fibers (or fiber segments) may be bonded, and thus they may serve as building blocks of "assembled structural elements" with a geometry different from that of the original fibers (or fiber segments). Such assembled structural elements include two-dimensional elements (or 2-dimensional structural elements), one-dimensional elements (or 1-dimensional structural elements), or zero-dimensional elements (or 0-dimensional structural elements).

As used herein, a two-dimensional structural element is referred to as having a length and width much greater than its thickness. In the present disclosure, the length and width of a two-dimensional structural element are greater than 2 times its thickness. An example of such an element is a "sheet". A one-dimensional structural element is referred to as having a length much greater than its width and thickness. In the present disclosure, the length of a one-dimensional structural element is greater than 2 times its width and thickness. An example of such an element is a "fiber". A zero-dimensional structural element is referred to as having a length and width of the order of its thickness. In the present disclosure, the length and width of a zero-dimensional structural element are no greater than 2 times its thickness. Furthermore, the thickness of a zero-dimensional element is less than 2.5 mm. Examples of such zero-dimensional elements are "particles" or "beads" and include polyhedra, spheroids, ellipsoids, or clusters thereof.

In the invention herein, any three dimensional structural framework comprising at least one structural element (e.g., a zero-dimensional, one-dimensional, or two-dimensional structural element) comprising an arrangement/assembly/assemblage of bonded fibers or bonded fiber segments is considered a three dimensional structural network of one or more fibers.

SCOPE OF THE INVENTION

It is contemplated that a particular feature described either individually or as part of an embodiment in this disclosure can be combined with other individually described features, or parts of other embodiments, even if the other features and embodiments make no mention of the particular feature. Thus, the invention herein extends to such specific combinations not already described. Furthermore, the drawings and embodiments of the invention herein have been presented as examples, and not as limitations. Thus, it is to be understood that the invention herein is not limited to these precise embodiments. Other embodiments apparent to those of ordinary skill in the art are within the scope of what is claimed.

By way of example but not by way of limitation, it is contemplated that compositions, systems, devices, methods, and processes of the claimed invention encompass variations and adaptations developed using information from the embodiments described herein. Adaptation and/or modification of the compositions, systems, devices, methods, and processes described herein may be performed by those of ordinary skill in the relevant art.

Furthermore, where compositions, articles, and devices are described as having, including, or comprising specific components, or where processes and methods are described as having, including, or comprising specific steps, it is contemplated that, additionally, there are compositions, articles, and devices of the present invention that consist essentially of, or consist of, the recited components, and that there are processes and methods according to the present invention that consist essentially of, or consist of, the recited processing steps.

Similarly, where compositions, articles, and devices are described as having, including, or comprising specific compounds and/or materials, it is contemplated that, additionally, there are compositions, articles, and devices of the present invention that consist essentially of, or consist of, the recited compounds and/or materials.

It should be understood that the order of steps or order for performing certain action is immaterial so long as the invention remains operable. Moreover, two or more steps or actions may be conducted simultaneously.

The mention herein of any publication is not an admission that the publication serves as prior art with respect to any of the claims presented herein. Headers are provided for organizational purposes and are not meant to be limiting.

DETAILED DESCRIPTION OF THE INVENTION

Aspects of the Method

FIG. 1 presents a non-limiting example of a method of manufacturing pharmaceutical solid dosage forms according to this invention. At least one of each active ingredient 101, excipient 102, and solvent 103 are injected into the extrusion channel 105 of at least one first extruder 100, said channel 105 terminating at at least one exit port 120 having a valve 125. In the extrusion channel 105 the injected active ingredient 101, excipient 102, and solvent 103 are mixed to form a plasticized matrix. The plasticized matrix is conveyed to the first extruder's exit port 120 and extruded through said exit port 120 and the valve 125, thereby filling at least one extrusion channel 155 of at least one second extruder 150 with said extruded plasticized matrix. The second extruder channel 155 terminates at at least one fiber fabrication exit port 165, 166. The plasticized matrix in said second extruder 150 extrusion channel 155 is extruded through said fiber fabrication port 166 at a controlled speed, and the extruded plasticized fiber is deposited onto a fiber assembling stage 180 to a form a three dimensional fiber structural framework 185 defined by the motion of said stage 180 at the speed of the exiting extruded, plasticized fiber.

Generally, said valve 125 permits or allows flow of plasticized matrix from the extrusion channel 105 of said first extruder 100 into said at least one extrusion channel 155 of said at least one second extruder 150 while said second extruder's channel is filled with plasticized matrix. Moreover, generally, said valve 125 blocks or restricts or prevents flow of plasticized matrix from said at least one extrusion channel 155 of said at least one second extruder 150 into said first extruder's channel 105 while fiber is extruded through said fiber fabrication exit port 165, 166. A non-limiting example of a valve 125 that satisfies the above requirements is a check valve. A check valve may further be preferable because it can be passive and may not require actuators for performing the above functions.

Figure 2:
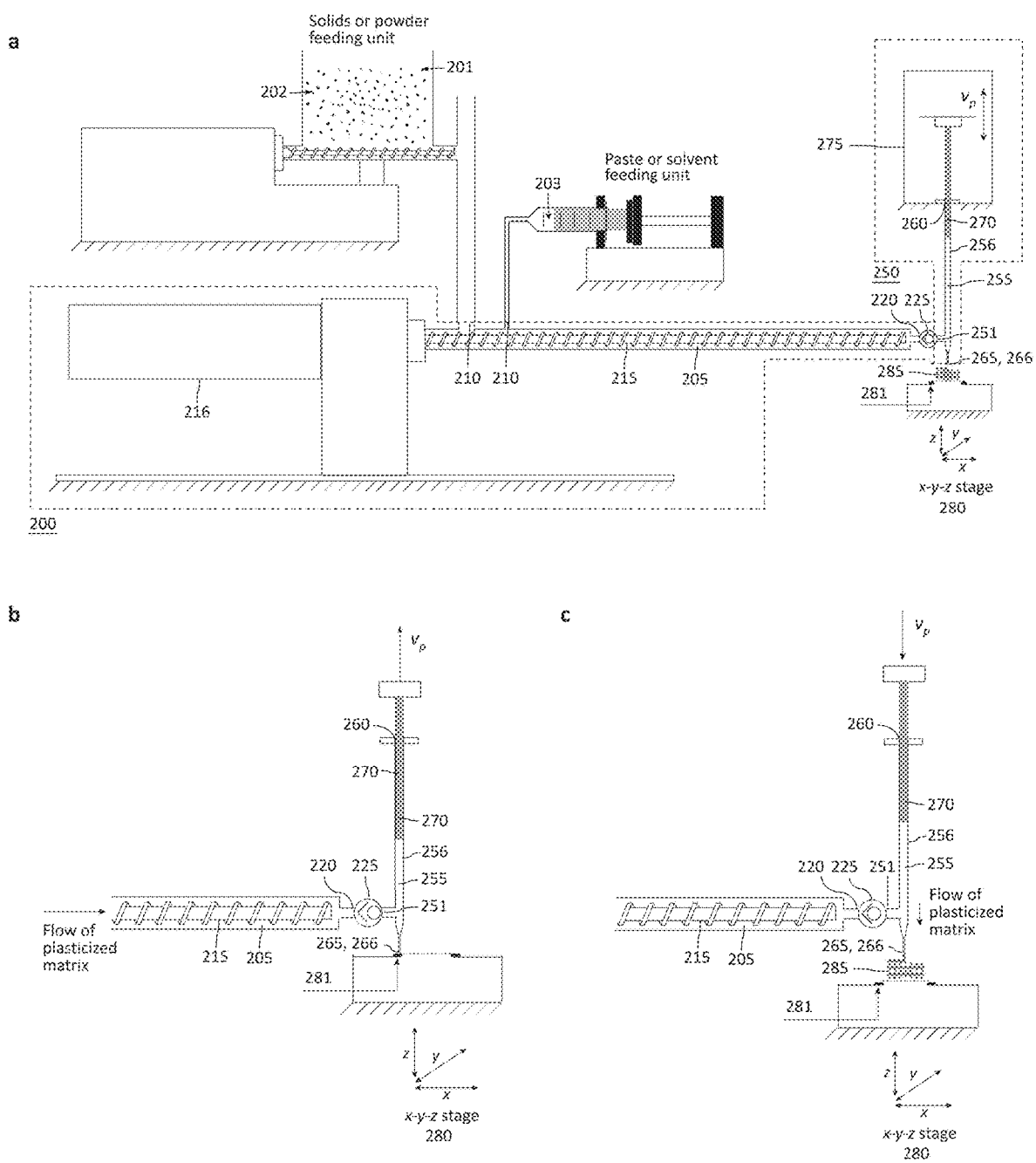
FIG. 2 illustrates another non-limiting example of an apparatus and a method according to this invention: (a) overview of the apparatus and method, (b) switching scheme of valves and actuators during filling of second extruder extrusion channel, and (c) switching scheme of valves and actuators during 3D-micro-patterning.

FIG. 2 presents another non-limiting example of a method of manufacturing pharmaceutical solid dosage forms according to this invention. At least one of each active ingredient 201, excipient 202, and solvent 203 are injected into the extrusion channel 205 of at least one first extruder 200, said channel 205 terminating at at least one exit port 220. Said exit port 220 having at least a check valve 225 mated to at least one input port 251 of at least one second extruder 250. In the first extruder's extrusion channel 205 the injected active ingredient 201, excipient 202, and solvent 203 are mixed to form a plasticized matrix. The plasticized matrix is conveyed to said first extruder's exit port 220 and extruded through said exit port 220 and the valve 225, thereby filling at least one extrusion channel 255 of at least one second extruder 250 with said extruded plasticized matrix. The second extruder channel 255 terminates at at least one fiber fabrication exit port 266. While plasticized matrix is extruded through the check valve 225 into the channel 255 of the second extruder a movable solid surface 281 is removably attached to the fiber fabrication exit port 266 to prevent or block flow of plasticized matrix through said fiber fabrication exit port 266. The movable solid surface 281 is then moved away from the fiber fabrication exit port 266 to allow flow of plasticized matrix through said fiber fabrication exit port 266. The plasticized matrix in said second extruder extrusion channel 255 is then extruded through said fiber fabrication port 266 at a controlled speed. The extruded plasticized fiber is deposited onto a fiber assembling stage 280 to form a three dimensional fiber structural framework 285 defined by the motion of said stage 280 at the speed of the exiting extruded, plasticized fiber.

Figure 3:
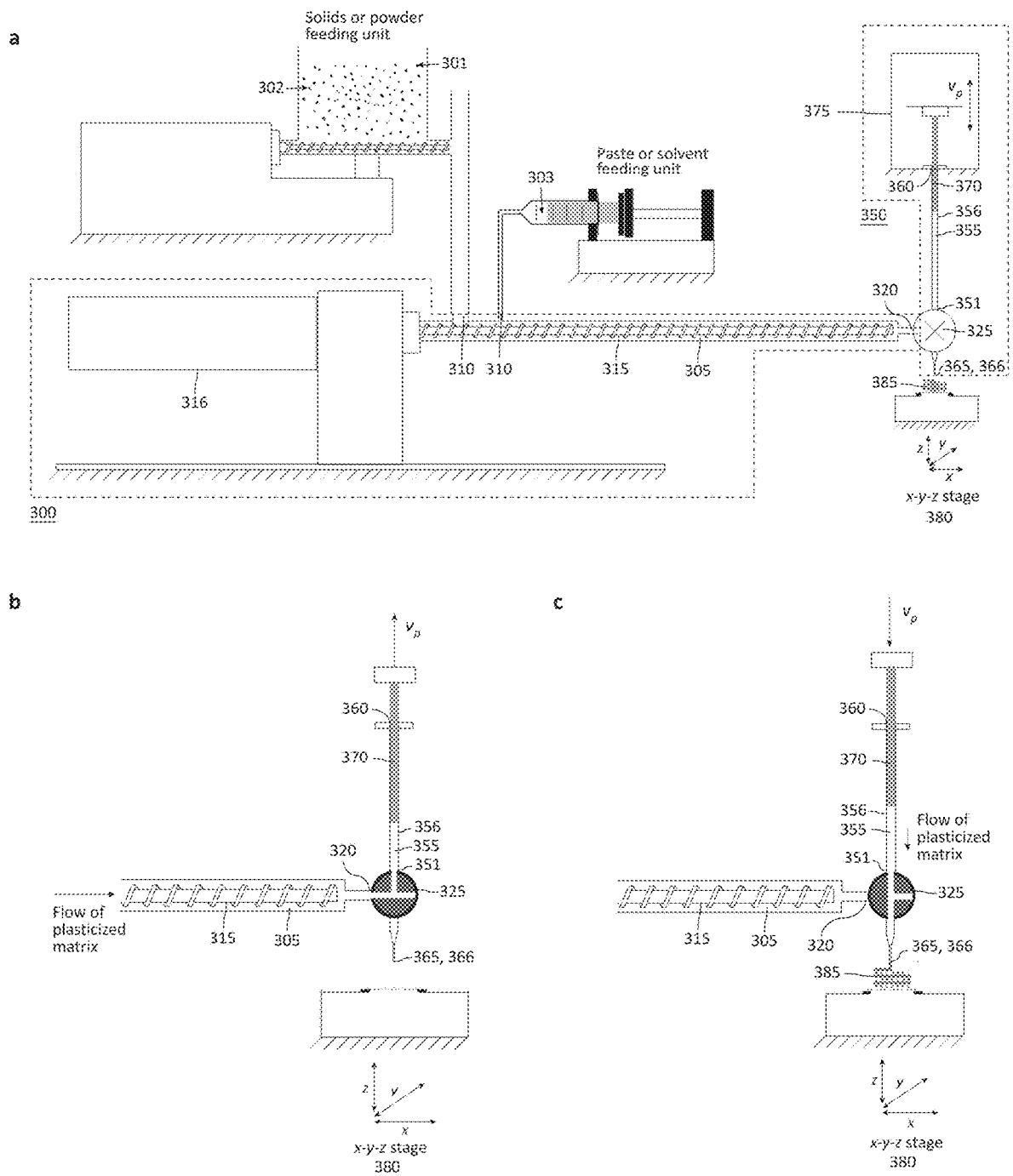
FIG. 3 schematically shows another a non-limiting apparatus and method according to the invention herein: (a) overview of the apparatus and method, (b) switching scheme of valves and actuators during filling of second extruder extrusion channel, and (c) switching scheme of valves and actuators during 3D-micro-patterning.

FIG. 3 presents another non-limiting example of a method of manufacturing pharmaceutical solid dosage forms according to this invention. At least one of each active ingredient 301, excipient 302, and solvent 303 are injected into the extrusion channel 305 of at least one first extruder 300, said channel 305 terminating at at least one exit port 320. Said exit port 320 having at least a three-way valve 325 mated to at least one input port 351 of at least one second extruder 350. In the extrusion channel 305 the injected active ingredient 301, excipient 302, and solvent 303 are mixed to form a plasticized matrix. The plasticized matrix is conveyed to said first extruder's exit port 320 and extruded through said exit port 320 and the three-way valve 325, thereby filling at least one extrusion channel 355 of at least one second extruder 350 with said extruded plasticized matrix. The second extruder channel 355 terminates at at least one fiber fabrication exit port 366. While plasticized matrix is extruded through the three-way valve 325 into the channel 355 of the second extruder the flow path of said three-way valve allows flow through the first extruder's exit port and into the channel of the second extruder and blocks or restricts flow from the first extruder's channel to the second extruder channel's exit port end 365, 366. The flow path of the three-way valve is then switched to allow flow of plasticized matrix through said fiber fabrication exit port 366, and to block or restrict flow from the second extruder's channel into the first extruder's channel. The plasticized matrix in said second extruder extrusion channel 355 is then extruded through said fiber fabrication port 366 at a controlled speed. The extruded plasticized fiber is deposited onto a fiber assembling stage 380 to form a three dimensional fiber structural framework 385 defined by the motion of said stage 380 at the speed of the exiting extruded, plasticized fiber.

Figure 4:
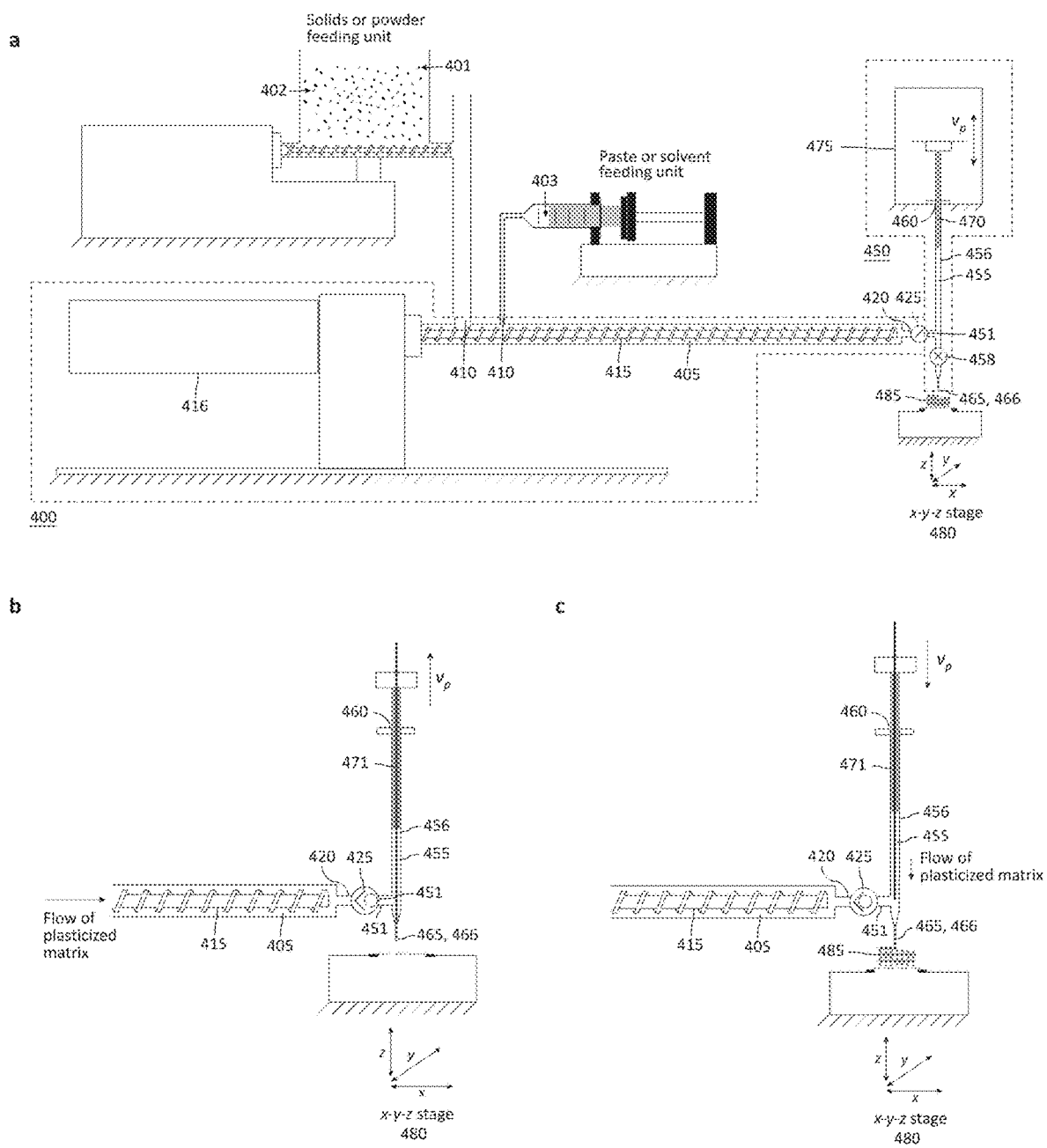
FIG. 4 presents another non-limiting apparatus and method according to this invention: (a) overview of the apparatus and method, (b) switching scheme of valves and actuators during filling of second extruder extrusion channel, and (c) switching scheme of valves and actuators during 3D-micro-patterning.

FIG. 4 presents another non-limiting example of a method of manufacturing pharmaceutical solid dosage forms according to this invention. At least one of each active ingredient 401, excipient 402, and solvent 403 are injected into the extrusion channel 405 of at least one first extruder 400, said channel 405 terminating at at least one exit port 420. Said exit port 420 having at least a first valve 425 mated to at least one input port 451 of at least one second extruder 450. In the extrusion channel 405 the injected active ingredient 401, excipient 402, and solvent 403 are mixed to form a plasticized matrix. The plasticized matrix is conveyed to said first extruder's exit port 420 and extruded through said exit port 420 and the first valve 425, thereby filling at least one extrusion channel 455 of at least one second extruder 450 with said extruded plasticized matrix. The second extruder channel 455 terminates at least one fiber fabrication exit port 466 and further comprises a second valve 458 between the input port 451 and the fiber fabrication exit port 466 of the at least one second extruder 450. While plasticized matrix is extruded through the first valve 425 into the channel of the second extruder 455 the second valve 458 prevents or blocks or restricts flow of plasticized matrix through said fiber fabrication exit port 466. The plasticized matrix in said second extruder extrusion channel 455 is then extruded through said fiber fabrication port 466 at a controlled speed while the first valve 425 blocks or restricts flow of plasticized matrix from the second extruder's channel 455 into the first extruder's channel 405 and the second valve 458 allows flow of plasticized matrix through said fiber fabrication exit port 466. The extruded plasticized fiber is deposited onto a fiber assembling stage 480 to form a three dimensional fiber structural framework 485 defined by the motion of said stage 480 at the speed of the exiting extruded, plasticized fiber. In some embodiments, said second valve 458 may comprise a a shutoff valve. By way of example but not by way of limitation, said shutoff valve may comprise a pin 471 or plug to block or prevent or restrict flow of plasticized matrix through a fiber fabrication exit port 466.

Figure 5:
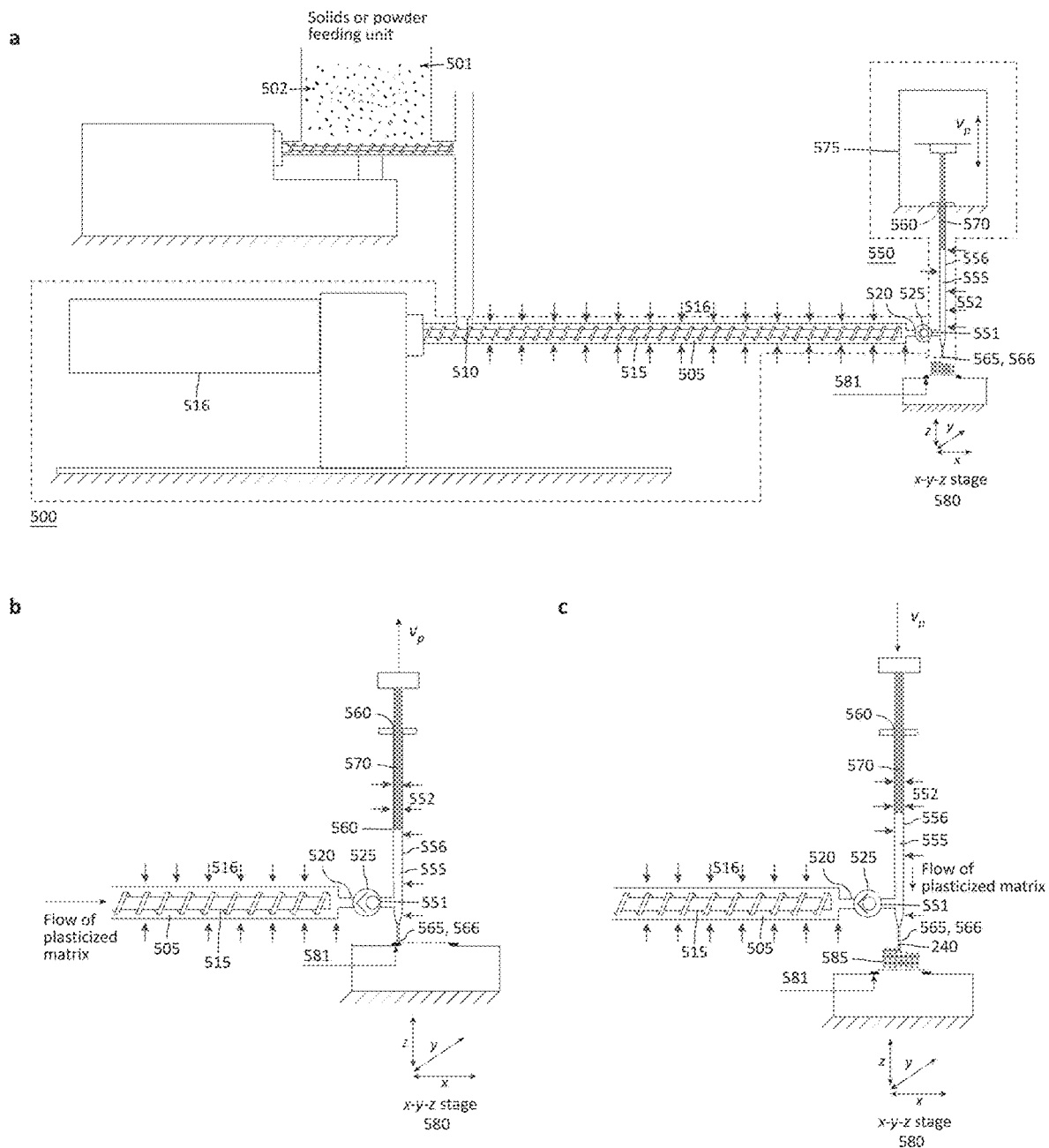
FIG. 5 presents another non-limiting apparatus and method for producing dosage forms according to this invention: (a) overview of the apparatus and method, (b) switching scheme of valves and actuators during filling of second extruder extrusion channel, and (c) switching scheme of valves and actuators during 3D-micro-patterning.

FIG. 5 presents another non-limiting example of a method of manufacturing pharmaceutical solid dosage forms according to this invention. At least one active ingredient 501 and at least one excipient 502 that melts upon heating are injected into the extrusion channel 505 of at least one first extruder 500, said extrusion channel 505 terminating at at least one exit port 520 having a valve 525. In the extrusion channel 505 the injected active ingredient 501 and excipient 502 are mixed and heated to form a plasticized matrix. The plasticized matrix is conveyed to the first extruder's exit port 520 and extruded through said exit port 520 and the valve 525, thereby filling at least one extrusion channel 555 of at least one second extruder 550 with said extruded plasticized matrix. The second extruder channel 555 terminates at at least one fiber fabrication exit port 565, 566. The plasticized matrix in said second extruder 550 extrusion channel 555 is extruded through said fiber fabrication exit port 566 at a controlled speed, and the extruded plasticized fiber is deposited onto a fiber assembling stage 580 to a form a three dimensional fiber structural framework 585 defined by the motion of said stage 580 at the speed of the exiting extruded, plasticized fiber.

Generally, said valve 525 permits or allows flow of plasticized matrix from the extrusion channel 505 of said first extruder 500 into said at least one extrusion channel 555 of said at least one second extruder 550 while said second extruder's channel is filled with plasticized matrix. Moreover, generally, said valve 525 blocks or restricts or prevents flow of plasticized matrix from said at least one extrusion channel 555 of said at least one second extruder 550 into said first extruder's channel 505 while fiber is extruded through said fiber fabrication exit port 565, 566. A non-limiting example of a valve 525 that satisfies the above requirements is a check valve. A check valve may further be preferable because it can be passive and may not require actuators for performing the above functions.

In some preferred embodiments, moreover, the non-limiting method illustrated in FIG. 5 may further comprise removably attaching a movable solid surface 581 to the fiber fabrication exit port 566 to prevent or block flow of plasticized matrix through said fiber fabrication exit port 566 while plasticized matrix is extruded through the check valve 525 into the channel 555 of the second extruder. In preferred embodiments, furthermore, the method may further comprise moving the movable solid surface 581 away from the fiber fabrication exit port 566 to allow flow of plasticized matrix through said fiber fabrication exit port 566.

It may be noted that in any method or apparatus disclosed herein, the drug (e.g., one or more drugs), and/or the excipient (e.g., one or more excipients), and/or the solvent (e.g., one or more solvents) may be fed or injected into an extrusion channel (e.g., the extrusion channel of a first extruder) using either one or any combinations of the following: one or more solids feeding units, such as one or more granular solids feeding units or one or more powder feeding units; one or more liquid feeding units, such as one or more solvent feeding units; one or more plasticized matrix feeding units; and so on. Thus, the drug and/or excipient can be injected or fed into the first extruder's channel as a solid, such as a granular solid or a powder; and/or as a liquid; and/or as dissolved molecules, dispersed particles, etc. in a liquid or paste; and/or as a plasticized matrix or paste, such as a drug and/or excipient plasticized by melting (e.g., drug and/or excipient at a temperature greater than their/its melting temperature) or a drug and/or excipient plasticized by solvation (e.g., by combining or mixing with a solvent); and so on.

It may be noted, moreover, that in any method or apparatus disclosed herein, drug (e.g., one or more drugs), and/or excipient (e.g., one or more excipients), and/or solvent (e.g., one or more solvents) can be injected or fed into an extrusion channel as a single component without any prior mixing. In some embodiments, however, drug (e.g., one or more drugs), and/or excipient (e.g., one or more excipients), and/or solvent (e.g., one or more solvents) may be mixed prior to injecting or feeding into the extrusion channel of the first extruder. By way of example but not by way of limitation, drug, excipient, and solvent may be mixed to form a plasticized matrix prior to injecting or feeding into the extrusion channel of the first extruder. Said plasticized matrix may then be fed or injected into the extrusion channel of the first extruder. Moreover, by way of example but not by way of limitation, drug and excipient particles may be mixed prior to feeding or injecting into the first extruder extruder channel. The drug-excipient particulate mixture may then be injected or fed through a feeding port into the first extruder extrusion channel.

In some preferred embodiments, furthermore, plasticized matrix is conveyed to the first extruder's exit port 120, 220, 320, 420, 520 and extruded through said exit port 120, 220, 320, 420, 520 and the valve 125, 225, 325, 425, 525 using at least a screw 115, 215, 315, 415, 515 (e.g., a single screw, a twin screw, etc.). Said at least one screw may be rotatable 115, 215, 315, 415, 515, and driven by a motor 116, 216, 316, 416, 516, such as an electric motor.

Similarly, in some preferred embodiments, plasticized matrix in a second extruder extrusion channel 155, 255, 355, 455, 555 is extruded through a fiber fabrication exit port 166, 266, 366, 466, 566 of said second extruder extrusion channel 155, 255, 355, 455, 555 using a piston 170, 270, 370, 470, 570 that advances at a controlled speed towards said fiber fabrication exit port 166, 266, 366, 466, 566. The piston 170, 270, 370, 470, 570 may further be in contact with and/or enclosed by the channel walls 156, 256, 356, 456, 556 of the second extruder extrusion channel 155, 255, 355, 455, 555. The piston 170, 270, 370, 470, 570 may further be driven by an electric motor 175, 275, 375, 475, 575, such as a servo motor or a stepper motor.

Moreover, for precisely controlling the rate at which plasticized matrix is extruded from a second extruder extrusion channel 155, 255, 355, 455, 555 through one or more fiber fabrication exit ports 166, 266, 366, 466, 566, the number of fiber fabrication exit ports 166, 266, 366, 466, 566 of said second extruder extrusion channel 155, 255, 355, 455, 555 should be limited. In some preferred embodiments, therefore, a second extruder extrusion channel 155, 255, 355, 455, 555 may comprise no more than 10 fiber fabrication exit ports 166, 266, 366, 466, 566. This includes, but is not limited to a second extruder extrusion channel 155, 255, 355, 455, 555 comprising no more than 9, or no more than 8, or no more than 7, or no more than 6, or no more than 5, or no more than 4, or no more than 3, or no more than 2 fiber fabrication exit ports 166, 266, 366, 466, 566. Most preferably, for precisely controlling the speed of an extruded fiber, a second extruder extrusion channel 155, 255, 355, 455, 555 should comprise a single, or no more than one, fiber fabrication exit ports 166, 266, 366, 466, 566.

Because the number of fiber fabrication exit ports 166, 266, 366, 466, 566 of second extruder extrusion channels 155, 255, 355, 455, 555 may be limited, to speed up the production rate, the first extruder extrusion channel 105, 205, 305, 405, 505 may comprise multiple exit ports 120, 220, 320, 420, 520. Each said exit port 120, 220, 320, 420, 520 may have valve 125, 225, 325, 425, 525 and multiple (e.g., at least two) of said valves 125, 225, 325, 425, 525 may be mated to the input ports 151, 251, 351, 451, 551 of at least two second extruders 150, 250, 350, 450, 550. In some embodiments, moreover, an extrusion channel of a first extruder bifurcates into a plurality of exit ports. Each said exit port may have a valve.

It may be noted, moreover, that any sequence of steps described in the invention herein may be performed concurrently (e.g., at least one step is performed at the same time as another step) or in sequence (e.g., one step is performed at a time and a subsequent step starts after completion of a previous step). In addition, any process step described with respect to one aspect of the invention can be applied with respect to another aspect. By way of example but not by way of limitation, a solid constituent (e.g., an excipient, a drug, etc.) may be plasticized by a combination of solvation (e.g., mixing or combining with a solvent) and melting.

Any more examples of the process steps to manufacture the fibrous dosage forms would be obvious to a person of ordinary skill in the art. All of them are within the scope of this invention.

Aspects of the Apparatus

FIG. 1 also presents a non-limiting example of an apparatus for manufacturing pharmaceutical solid dosage forms according to this invention. The apparatus comprises at least one first extruder 100 and at least one second extruder 150. Said first extruder 100 comprises an extrusion channel 105 with one or more feeding ports 110 for injecting drug, excipient, and solvent into the extrusion channel 105, and means for forming and extruding a plasticized matrix 115 therein. Said first extruder channel 105 terminates at at least one exit port 120. Said at least one exit port 120 having a valve 125, said valve 125 mated to at least one input port 151 of at least one second extruder 150.

Said second extruder 150 comprises its own extrusion channel 155 defined by channel walls 156, the channel 155 having a closed first end 160 and a second exit port end 165. The channel walls 156 are in contact with and enclose a piston 170 translatable along the channel's 155 longitudinal axis between said first 160 and second ends 165. Said piston 170 recedes towards said first end 160 upon filling of the extrusion channel 155 with plasticized matrix from the first extruder 100. The second extruder 150 further comprises means for translating or advancing the piston 175 towards the second end 165 and thereby conveying the plasticized matrix at a controlled speed towards the second end 165, wherein said second end 165 terminates in a fiber fabrication exit port 166 for extruding the conveyed plasticized matrix and manufacturing the dosage forms.

The apparatus further comprises a translating or rotating stage 180 movable in the x, y, and z directions at the controlled speed of the exiting extruded, plasticized fiber, whereby the exiting fiber can be assembled into a three dimensional structural framework 185 by depositing said fiber along a path defined by motion of said stage 180.

Generally, said valve 125 permits or allows flow of plasticized matrix from the extrusion channel 105 of said first extruder 100 into said at least one extrusion channel 155 of said at least one second extruder 150 while said second extruder's channel is filled with plasticized matrix. Moreover, generally, said valve 125 blocks or restricts or prevents flow of plasticized matrix from said at least one extrusion channel 155 of said at least one second extruder 150 into said first extruder's channel 105 while fiber is extruded through said fiber fabrication exit port 165, 166. A non-limiting example of a valve 125 that satisfies the above requirements is a check valve. A check valve may further be preferable because it can be passive and may not require actuators for performing the above functions.

FIG. 2 also presents another non-limiting example of an apparatus for manufacturing pharmaceutical solid dosage forms according to this invention. The apparatus comprises at least one first extruder 200 and at least one second extruder 250. The first extruder 200 comprises an extrusion channel 205 with feeding ports 210 for injecting drug, excipient, and solvent into the extrusion channel 205, and one or more rotatable screws 215 for forming and extruding a plasticized matrix therein. The channel 205 terminates at at least one exit port 220. Said at least one exit port 220 having a check valve 225, said check valve 225 mated to at least one input port 251 of at least one second extruder 250.

Said second extruder 250 comprises its own extrusion channel 255 defined by channel walls 256, the channel 255 having a closed first end 260 and a second exit port end 265. The channel walls 256 are in contact with and enclose a piston 270 translatable along the channel's 255 longitudinal axis between said first 260 and second ends 265. Said piston 270 recedes towards said first end 260 upon filling of the extrusion channel 255 with plasticized matrix from the first extruder 200. The second extruder 250 further comprises an electric motor 275 for translating or advancing the piston 270 towards the second end 265 and thereby conveying the plasticized matrix at a controlled speed towards the second end 265, said second end 265 terminating in a fiber fabrication exit port 266 for extruding the conveyed plasticized matrix and manufacturing the dosage forms.

The apparatus further comprises a movable solid surface 281 removably attached to the fiber fabrication exit port 266 to flexibly block flow of plasticized matrix through the fiber fabrication exit port 266. The apparatus further comprises a translating or rotating stage 280 movable in the x, y, and z directions at the controlled speed of the exiting extruded, plasticized fiber, whereby the exiting fiber can be assembled into a three dimensional structural framework by depositing said fiber along a path defined by motion of said stage 280. In some preferred embodiments, the stage 280 also comprises the movable solid surface 281 (e.g., the movable solid surface 281 is attached to or included in the movable stage 280).

FIG. 3 also presents another non-limiting example of an apparatus for manufacturing pharmaceutical solid dosage forms according to this invention. The apparatus comprises at least one first extruder 300 and at least one second extruder 350. The first extruder 300 comprises an extrusion channel 305 with feeding ports 310 for injecting drug, excipient, and solvent into the extrusion channel 305, and one or more rotatable screws 315 for forming and extruding a plasticized matrix therein. The channel 305 terminates at at least one exit port 320. Said at least one exit port 320 having a three-way valve 325, said three-way valve 325 mated to at least one input port 351 of at least one second extruder 350.

Said second extruder 350 comprises its own extrusion channel 355 defined by channel walls 356, the channel 355 having a closed first end 360 and a second exit port end 365. The channel walls 356 are in contact with and enclose a piston 370 translatable along the channel's 355 longitudinal axis between said first 360 and second ends 365. Said piston 370 recedes towards said first end 360 upon filling of the extrusion channel 355 with plasticized matrix from the first extruder 300 while the flow path of said three-way valve allows flow through the first extruder's exit port and into the channel of the second extruder and blocks or restricts flow from the first extruder's channel to the second extruder channel's exit port end 365. The second extruder 350 further comprises an electric motor 375 for translating or advancing the piston 370 towards the second end 365 and thereby conveying the plasticized matrix at a controlled speed towards the second end 365 while the flow path of said three-way valve blocks or restricts flow from the channel of the second extruder through the first extruder's exit port and allows flow through the second extruder's channel and through its second end 365, so that said second end 365 terminates in a fiber fabrication exit port 366 for extruding the conveyed plasticized matrix and manufacturing the dosage forms.

The apparatus further comprises a translating or rotating stage 380 movable in the x, y, and z directions at the controlled speed of the exiting extruded, plasticized fiber, whereby the exiting fiber can be assembled into a three dimensional structural framework by depositing said fiber along a path defined by motion of said stage 380.

FIG. 4 also presents another non-limiting example of an apparatus for manufacturing pharmaceutical solid dosage forms according to this invention. The apparatus comprises at least one first extruder 400 and at least one second extruder 450. The first extruder 400 comprises an extrusion channel 405 with feeding ports 410 for injecting drug, excipient, and solvent into the extrusion channel 405, and one or more rotatable screws 415 for forming and extruding a plasticized matrix therein. The channel 405 terminates at at least one exit port 420. Said at least one exit port 420 having a first valve 425, said first valve 425 mated to at least one input port 451 of at least one second extruder 450.

Said second extruder 450 comprises its own extrusion channel 455 defined by channel walls 456, the channel 455 having a closed first end 460 and a second exit port end 465 and a second valve 458 between said input 451 port and said second end 465. The channel walls 456 are in contact with and enclose a piston 470 translatable along the channel's 455 longitudinal axis between said first 460 and second ends 465. Said piston 470 recedes towards said first end 460 upon filling of the extrusion channel 455 with plasticized matrix from the first extruder 400 while the first valve 425 allows flow through the first extruder's exit port 420 and into the channel of the second extruder 455 and the second valve 458 blocks or restricts flow from the first extruder's channel 405 to the second extruder channel's exit port end 465. The second extruder 450 further comprises an electric motor 475 for translating or advancing the piston 470 towards the second end 465 and thereby conveying the plasticized matrix at a controlled speed towards the second end 465 while the first valve 425 blocks flow from the channel of the second extruder 455 through the first extruder's exit port 420 and the second valve 458 allows flow through the second extruder's channel 455 and through its second end 465, so that said second end 465 terminates in a fiber fabrication exit port 466 for extruding the conveyed plasticized matrix and manufacturing the dosage forms.

The apparatus further comprises a translating or rotating stage 480 movable in the x, y, and z directions at the controlled speed of the exiting extruded, plasticized fiber, whereby the exiting fiber can be assembled into a three dimensional structural framework 485 by depositing said fiber along a path defined by motion of said stage 480.

FIG. 5 also presents a non-limiting example of an apparatus for manufacturing pharmaceutical solid dosage forms according to this invention. The apparatus comprises at least one first extruder 500 and at least one second extruder 550. Said first extruder 500 comprises an extrusion channel 505 with one or more feeding ports 510 for injecting drug and excipient into the extrusion channel 505, wherein at least one excipient melts upon heating. Said first extruder 500 further comprises at least one heating element 516 for forming a plasticized matrix 515 therein, and means for extruding plasticized matrix 515 through the extrusion channel 505. Said first extruder channel 505 terminates in at least one exit port 520. Said at least one exit port 520 having a valve 525, said valve 525 mated to at least one input port 551 of at least one second extruder 550.

Said second extruder 550 comprises its own extrusion channel 555 defined by channel walls 556, the channel 555 having a closed first end 560 and a second exit port end 565. The channel walls 556 are in contact with and enclose a piston 570 translatable along the channel's 555 longitudinal axis between said first 560 and second ends 565. Said piston 570 recedes towards said first end 560 upon filling of the extrusion channel 555 with plasticized matrix from the first extruder 500. The second extruder 550 further comprises at least a heating element 552 to prevent premature solidification of the plasticized matrix therein. The second extruder 550 further comprises means for translating or advancing the piston 575 towards the second end 565 and thereby conveying the plasticized matrix at a controlled speed towards the second end 565, wherein said second end 565 terminates in a fiber fabrication exit port 566 for extruding the conveyed plasticized matrix and manufacturing the dosage forms.

The apparatus further comprises a translating or rotating stage 580 movable in the x, y, and z directions at the controlled speed of the exiting extruded, plasticized fiber, whereby the exiting fiber can be assembled into a three dimensional structural framework 585 by depositing said fiber along a path defined by motion of said stage 580.

Generally, said valve 525 permits or allows flow of plasticized matrix from the extrusion channel 505 of said first extruder 500 into said at least one extrusion channel 555 of said at least one second extruder 550 while said second extruder's channel 555 is filled with plasticized matrix. Moreover, generally, said valve 525 blocks or restricts or prevents flow of plasticized matrix from said at least one extrusion channel 555 of said at least one second extruder 550 into said first extruder's channel 505 while fiber is extruded through said fiber fabrication exit port 565, 566. A non-limiting example of a valve 525 that satisfies the above requirements is a check valve. A check valve may further be preferable because it can be passive and may not require actuators for performing the above functions.

In some preferred embodiments, the apparatus further comprises a movable solid surface 581 removably attached to the fiber fabrication exit port 566 to flexibly block flow of plasticized matrix through the fiber fabrication exit port 566. In some preferred embodiments, moreover, the stage 580 also comprises the movable solid surface 581 (e.g., the movable solid surface 581 is attached to or included in the movable stage 580).

It may be noted that any apparatus or method herein may further comprise one or more solids feeding units, such as one or more granular solids feeding units or one or more powder feeding units for feeding or injecting solid drug and/or excipient (e.g., in the form of a granular solid, in the form of a powder, etc.) through one or more feeding ports 110, 210, 310, 410, 510 into the first extruder extrusion channel 105, 205, 305, 405, 505.

Moreover, any apparatus or method herein may further comprise one or more liquid or solvent feeding units for injecting or feeding one or more liquids or solvents with or without dissolved or dispersed drug and/or excipient through one or more feeding ports 110, 210, 310, 410, 510 into the first extruder extrusion channel 105, 205, 305, 405, 505.

Moreover, any apparatus or method herein may further comprise one or more plasticized matrix feeding units for injecting or feeding plasticized matrix (e.g., drug and/or excipient at a temperature greater than their/its melting temperature, drug and/or excipient plasticized by solvation, etc.) through one or more feeding ports 110, 210, 310, 410, 510 into the first extruder extrusion channel 105, 205, 305, 405, 505.

In some preferred embodiments, furthermore, plasticized matrix is conveyed to the first extruder's exit port 120, 220, 320, 420, 520 and extruded through said exit port 120, 220, 320, 420, 520 and the valve 125, 225, 325, 425, 525 using at least a screw 115, 215, 315, 415, 515 (e.g., a single screw, a twin screw, etc.). Said at least one screw may be rotatable 115, 215, 315, 415, 515, and may, for example, be driven by a motor 116, 216, 316, 416, 516, such as an electric motor.

Similarly, in some preferred embodiments, a piston 170, 270, 370, 470, 570 that advances at a controlled speed towards said fiber fabrication exit port 166, 266, 366, 466, 566 may be driven by an electric motor 175, 275, 375, 475, 575, such as a servo motor or a stepper motor.

Moreover, for precisely controlling the rate at which plasticized matrix is extruded from a second extruder extrusion channel 155, 255, 355, 455, 555 through one or more fiber fabrication exit ports 166, 266, 366, 466, 566, the number of fiber fabrication exit ports 166, 266, 366, 466, 566 of said second extruder extrusion channel 155, 255, 355, 455, 555 should be limited. In some preferred embodiments, therefore, a second extruder extrusion channel 155, 255, 355, 455, 555 may comprise no more than 10 fiber fabrication exit ports 166, 266, 366, 466, 566. This includes, but is not limited to a second extruder extrusion channel 155, 255, 355, 455, 555 comprising no more than 9, or no more than 8, or no more than 7, or no more than 6, or no more than 5, or no more than 4, or no more than 3, or no more than 2 fiber fabrication exit ports 166, 266, 366, 466, 566. Most preferably, for precisely controlling the speed of an extruded fiber, a second extruder extrusion channel 155, 255, 355, 455, 555 should comprise a single, or no more than one, fiber fabrication exit ports 166, 266, 366, 466, 566.

Because the number of fiber fabrication exit ports 166, 266, 366, 466, 566 of second extruder extrusion channels 155, 255, 355, 455, 555 may be limited, to speed up the production rate, the first extruder extrusion channel 105, 205, 305, 405, 505 may comprise multiple exit ports 120, 220, 320, 420, 520. Each said exit port 120, 220, 320, 420, 520 may have a valve 125, 225, 325, 425, 525 and multiple (e.g., at least two) of said valves 125, 225, 325, 425, 525 may be mated to the input ports 151, 251, 351, 451, 551 of at least two second extruders 150, 250, 350, 450, 550. In some embodiments, moreover, an extrusion channel of a first extruder bifurcates into a plurality of exit ports. Each said exit port may have a valve.

Any more examples of apparatuses to manufacture the fibrous dosage forms would be obvious to a person of ordinary skill in the art. All of them are within the scope of this invention.

Process Models

The following examples present non-limiting ways by which the disclosed process may be modeled. The models and examples will enable one of skill in the art to more readily understand the details and advantages of the invention. The models and examples are for illustrative purposes only, and are not meant to be limiting in any way.

Figure 6:
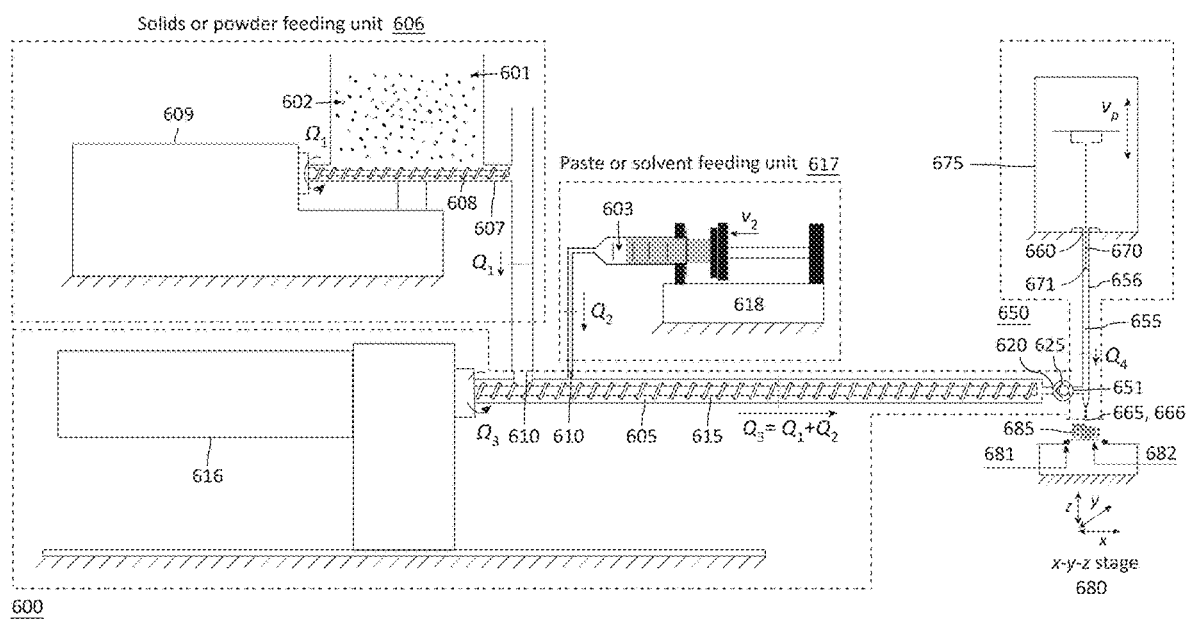
FIG. 6 is a schematic of the non-limiting apparatus and method used in the non-limiting process models.
Figure 7:
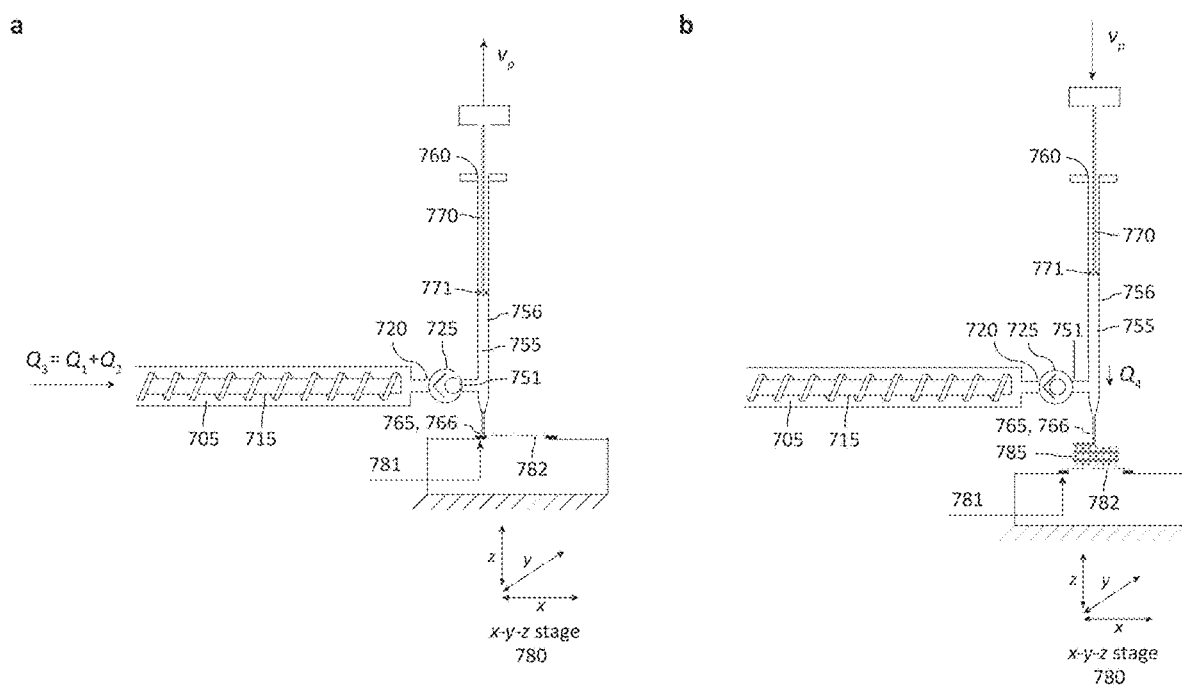
FIG. 7 schematically shows a non-limiting switching scheme of valves and actuators for producing dosage forms by the apparatus and method used in the non-limiting process models: (a) filling of second extruder extrusion channel, and (b) 3D-micro-patterning.
Figure 8:
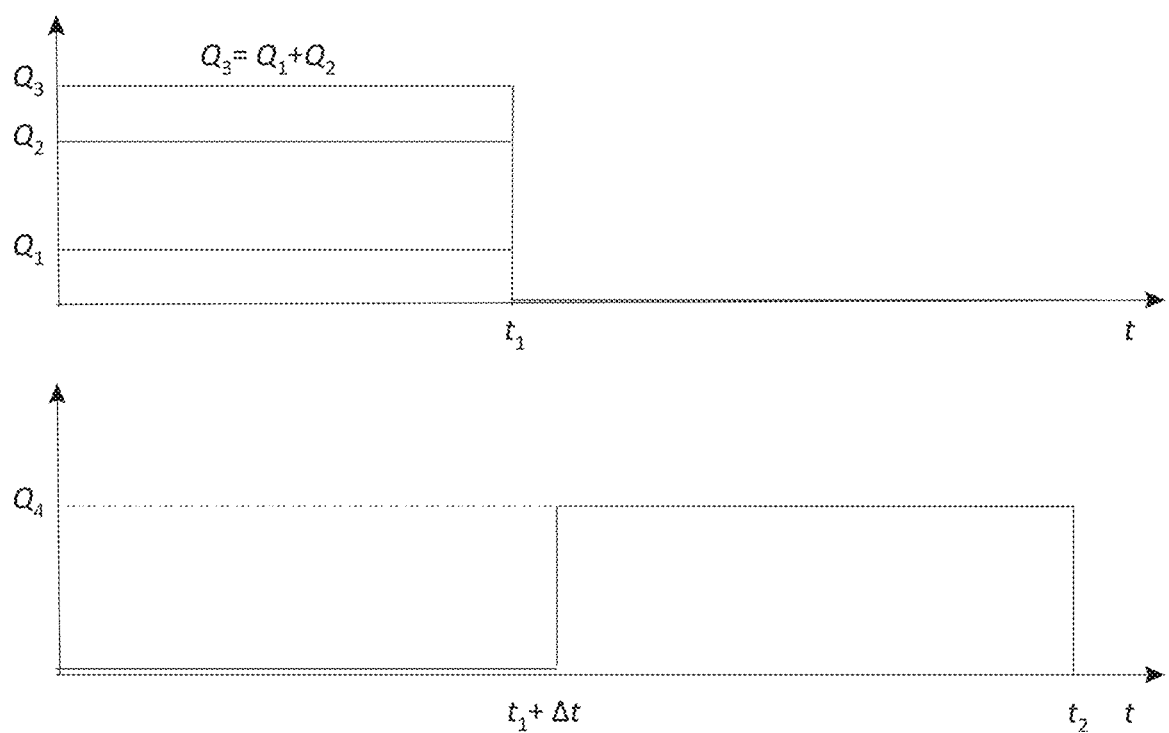
FIG. 8 schematically shows non-limiting flow rates in various sections of the apparatus while producing the dosage forms: (top) flow rates during filling of second extruder extrusion channel, and (bottom) flow rates during 3D-micro-patterning.

(a) Overview of the Apparatus and the Process for Manufacturing the Dosage Forms FIG. 6 is a non-limiting schematic of the process modeled here. The switching scheme of the relevant valves or actuators is shown in FIG. 7. The volumetric flow rates in various parts of the system and at various times are illustrated in FIG. 8.

As shown in FIG. 6, the apparatus includes a powder feeding unit 606 comprising at least a powder feeding extrusion channel 607 and two rotatable powder feeding screws 608 (e.g., a "twin screw") driven by at least an electric motor 609. (For simplicity only single screws are shown in the schematics). The apparatus further includes a first extruder 600 comprising an extrusion channel 605 with feeding ports 610 for injecting drug, excipient, and solvent into the extrusion channel 605, and one or more rotatable screws 615 driven by an electric motor 616 for forming and extruding a plasticized matrix therein. The channel 605 terminates at at least one exit port 620. Each said exit port 620 has a check valve 625. The apparatus further includes a liquid or paste feeding unit 617 comprising a pump for dispensing liquids or pastes 618 into the first extruder extrusion channel 605 at a controlled flow rate. In the non-limiting example of FIG. 6, the paste feeding pump 618 comprises a positive displacement pump.

The apparatus further includes at least a second extruder 650. Said second extruder 650 comprises its own extrusion channel 655 defined by channel walls 656, the channel 655 having at least an input port 651 mated to a check valve 625 at the exit port 620 of the first extruder extrusion channel 605, and a closed first end 660 and a second end 665 terminating in a fiber fabrication exit port 666. The channel's 655 cross sectional area (or the channel radius) contracts or tapers down before the fiber fabrication exit port 666 to the cross sectional area of said fiber fabrication exit port 666. The channel walls 656 are in contact with and enclose a piston 670 translatable along the channel's 655 longitudinal axis between said first end 660 and said input port of the second extruder extrusion channel 651. Said piston 670 comprises a seal 671 around its circumference to prevent or block flow of plasticized matrix through the first end 660 of the second extruder extrusion channel 655. The second extruder 650 further comprises an electric motor 675 for translating the piston 670.

The apparatus further comprises a translating or rotating stage 680 movable in x, y, and z directions at the controlled speed of the extruded plasticized fiber. The translating or rotating stage 680 includes a solid surface 681 for removably attaching to (or pressing towards) the channel walls of the fiber fabrication exit port 666 to flexibly block flow of plasticized matrix through said fiber fabrication exit port 666. The translating or rotating stage 680 further includes a deposition surface 682 for depositing and assembling fiber to form a three dimensional structural framework 685.

For manufacturing the dosage forms, the powder feeding unit 606 injects or feeds solid drug particles 601 into the extrusion channel 605 of the first extruder 600 at a controlled flow rate, $Q_1$. Concomitantly, the liquid or paste feeding unit 617 feeds or injects a viscous paste 603 of excipient and solvent into the first extruder's extrusion channel 605 at a rate $Q_2$. In the first extruder extrusion channel 605 the injected drug particles 601 are conveyed forward along the channel 605 with the rotating screws 615 and combined with the injected excipient-solvent paste 603. The particles 601 and the paste 603 are then mixed to form a plasticized matrix, and conveyed forward along the channel 605 by the rotating screws 615 at a rate $Q_3$. The plasticized matrix is conveyed to said first extruder's exit port 620 and extruded through said exit port 620 and the check valve 625, thereby filling at least one extrusion channel 655 of at least one second extruder 650 with said extruded plasticized matrix.

As shown schematically in the non-limiting FIGS. 6 and 7a, the piston 670, 770 of said second extruder recedes towards the first end 660, 760 of said second extruder extrusion channel 655, 755 upon filling of said extrusion channel 655, 755 with plasticized matrix from the first extruder's extrusion channel 605, 705. Moreover, while plasticized matrix is extruded through the check valve 625, 725 into the channel 655, 755 of the second extruder 650, 750 a movable solid surface 681, 781 is removably attached to (e.g., pressed to) the fiber fabrication exit port 666, 766 to prevent or block flow of plasticized matrix through said fiber fabrication exit port 666, 766.

Once the second extruder extrusion channel 655, 755 is sufficiently filled, the rotation rate of the powder feeding screws, $\Omega_1$, the displacement speed of the positive displacement paste feeding pump, $v_2$, and the rotation rate, $\Omega_3$, of the first extruder extrusion screws 615, 715 are dropped to zero or essentially zero, so that the flow rates $Q_1$, $Q_2$, and $Q_3$ drop to zero or essentially zero, and powder feeding, paste feeding, and extrusion through the first extruder are stopped, FIGS. 6, 7b and 8. The movable solid surface 681, 781 is moved away from the fiber fabrication exit port 666, 766 to allow flow of plasticized matrix through said fiber fabrication exit port 666, 766, and the deposition surface 682, 782 of the x-y-z stage 680, 780 is brought in line with said fiber fabrication exit port 666, 766. The check valve 625, 725 closes to prevent or block or restrict flow of plasticized matrix from the second extruder extrusion channel 655, 755 into the first extruder's extrusion channel 605, 705, and plasticized matrix in said second extruder extrusion channel 655, 770 is extruded through said fiber fabrication port 666, 766 at a controlled flow rate, $Q_4$, by advancing said piston 670, 770 with an electric motor 675 at a controlled speed towards said fiber fabrication port 666, 766.

The extruded plasticized fiber is deposited onto a fiber assembling stage 680, 780 to form a three dimensional fiber structural framework 685 defined by the motion of said stage 680, 780 at the speed of the exiting extruded, plasticized fiber.

Eventually, the second extruder extrusion channel 685 may be empty, and may need to be refilled by the mixture in the first extruder 600. The cycle of filling the second extruder extrusion channel 655 and depositing (or patterning) fiber on a fiber assembling stage 680 may be repeated until the desired fiber mass is deposited or patterned.

After (and/or during) depositing or patterning, the deposited structural framework 685 is solidified by evaporating the solvent. Moreover, in some embodiments a dosage form or a drug-containing solid may eventually be punched out from the patterned structure 685.

(b) Powder Feeding into the First Extruder

In the non-limiting process modeled here, the input drug is a powder, and is dispensed with a twin-screw powder feeder into the first extruder at a volumetric flow rate, $Q_1$. Powder flow in the complex setting of a twin-screw feeder has so far not been fully understood; thus the derivation of a closed-form solution of $Q_1$ is far beyond the scope of this disclosure. For engineering purposes, however, the following assumptions may be made: (a) the flow rate by the twin-screw powder feeder is twice that by a single screw, and (b) the velocity profile of the powder bed in the screw channel is linear, as in Couette flow.

Figure 9:
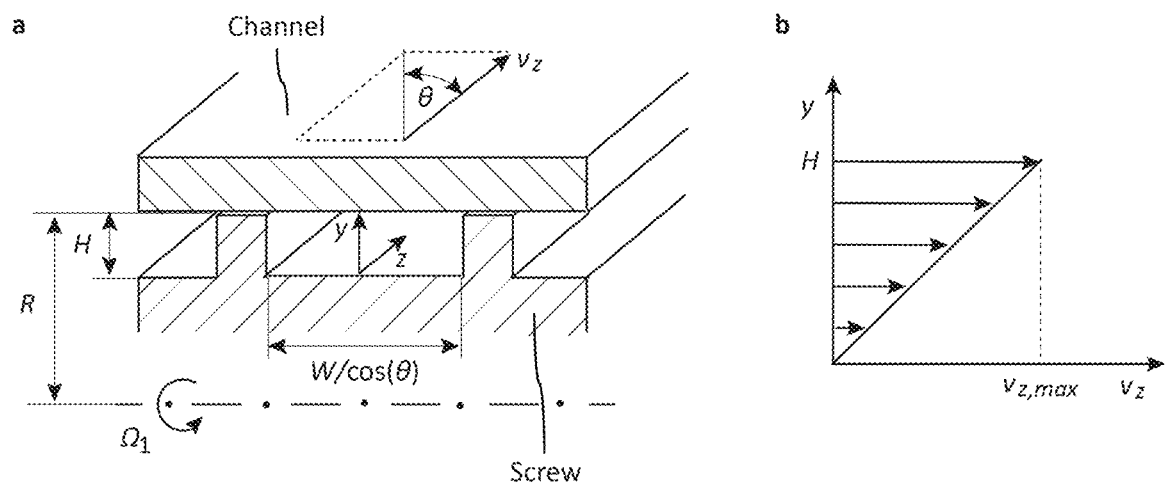
FIG. 9 presents a non-limiting example of an extrusion channel cross section and a screw that may be used in an apparatus or method of this invention.

For a twin screw with rectangular channel, as shown schematically in the non-limiting FIG. 9, the flow rate through the powder feeder, $Q_1$, may be written as:

$$Q_1 = \varphi_{part} H_1 W_1 \Omega_1 R_1 \cos(\theta) \quad (1)$$

where $\varphi_{part}$ the volume fraction of particles in the powder bed, $H_1$ the height and $W_1$ the width of the screw channel, $R_1$ is the outer radius of the screw (inner radius of the barrel or powder feeder's extrusion channel), $\Omega_1$ the angular velocity of the screw with respect to the barrel, and $\theta$ the helix angle of the screw.

For the non-limiting parameters $\varphi_{part}=0.3$, $H_1=1.5$ mm, $W_1=4.5$ mm, $R_1=4.5$ mm, $\theta=17°$, and $\Omega_1=0.45$ rad/s, by Eq. (1) the flow rate, $Q_1=3.9$ mm³/s. $Q_1$ may be readily adjusted, however, by changing the angular velocity, $\Omega_1$.

(c) Paste Feeding into the First Extruder

The excipient-solvent paste, the other input, may be fed into the first extruder with a syringe driven by a syringe pump. Because the paste is incompressible, the flow rate of the paste, $\Omega_2$, may be obtained from the simple equation:

$$Q_2 = A_2 v_2 \quad (2)$$

where $A_2$ the cross sectional area of the syringe barrel and $v_2$ the velocity of the advancing piston.

Using the non-limiting parameters $A_2=167.4$ mm², $v_2=0.5$ mm/s, by Eq. (2) $\Omega_2=83.7$ mm³/s.

(d) Formation of a Homogeneous Mixture and Filling of the Second Extruder Extrusion Channel If the paste is highly viscous, the flow of the paste through the first extruder's extrusion channel may be laminar, and turbulences may not occur. Nonetheless, in the extrusion channel the paste and the drug particles may be mixed due to the velocity gradients across and along the extruder channel until a homogeneous mixture of drug, excipient, and solvent may be formed. In analogy to Eq. (1), assuming that (a) the volumetric flow rate due to the rotating twin screw is twice that of the rotating single screw, (b) the pressure gradient along the screw (or channel) is small so that drag flow prevails, and (c) the mixture (or plasticized matrix of drug, excipient, and solvent) is Newtonian viscous so that the flow profile between the barrel and the screw may be essentially linear, as in Couette flow, the flow rate of plasticized matrix through the extruder channel may be written as:

$$Q_3 = H_3 W_3 \Omega_3 R_3 \cos(\theta_3) \quad (3)$$

where $H_3$ is the height and $W_3$ the width of the screw channel, $R_3$ is the outer radius of the screw (inner radius of the barrel or first extruder's extrusion channel), $\theta_3$ the helix angle of the screw, and $\Omega_3$ the angular velocity of the screw.

At steady state, by mass conservation $Q_3=Q_1+Q_2$. Thus, for the non-limiting parameters, $H_3=2$ mm, $W_3=6$ mm, $R_3=6$ mm, $\theta=17°$, by Eq. (3) the flow rate, $Q_3=Q_1+Q_2=101$ mm³/s at $\Omega_3=1.5$ rad/s.

The time to fill the second extruder's extrusion channel may be written as:

$$t_{fill} = \frac{V_4}{Q_3} \quad (4)$$

where $V_4$ is the relevant volume of the second extruder's extrusion channel. For the flow rate above, a second extruder's extrusion channel of 0.5 ml (500 mm³) may be filled in about 5 seconds.

(e) Extrusion of Fibers by Extrusion Syringe

As soon as the second extruder's extrusion channel is sufficiently filled, the rotation of the screws of the first extruder may stop and the check valve at the first extruder extrusion channel's exit may close to block backflow from the second extruder channel into the first extruder. The piston enclosed by the channel walls of the second extruder channel may then be advanced towards the fiber fabrication exit port to extrude plasticized fiber at a precisely controlled flow rate, $Q_4$.

If the diameter of the fiber fabrication exit port is small and the paste is highly viscous, the force acting on the piston to drive fluid flow through the exit port can be substantial. The force may be expressed as:

$$F_4 = A_4 \Delta p_4 \quad (5)$$

where $A_4$ is the cross sectional area of the second extruder channel and $\Delta p_4$ the pressure drop in the nozzle.

The pressure drop is determined by the viscous flow resistance. In some cases, the viscosity of the paste can be described by a power law function:

$$\mu = m \dot{\gamma}^{n-1} \quad (6)$$

where m is a constant of dimension Pa·s$^n$ and n a dimensionless constant.

The pressure gradients may be greatest when the radius is smallest. Thus, considering only the section of the smallest radius, and neglecting the effect of the contractions, the pressure drop across the nozzle, $\Delta p_4$, for a power-law fluid may be expressed as:

$$\Delta p_4 = \frac{2(1/n+3)^n m Q_4^n L_4}{\pi^n R_4^{3n+1}} \quad (7)$$

where $R_4$ the radius and $L_4$ the length of the narrow section of the nozzle.

Finally, the flow rate, $\Omega_4$, should be so balanced that the velocity of the extruded fiber is the same as the velocity of the translating stage on which the fiber is deposited. Thus:

$$Q_4 = \pi R_4^2 v_{st} \quad (8)$$

where $v_{st}$ is the velocity of the translating stage. For the non-limiting parameters $R_4=175$ μm and $v_{st}=10$ mm/s, by Eq. (8) $Q_4=0.96$ mm³/s.

Substituting this flow rate into Eq. (5) the force acting on the piston can be calculated. It is evident that the cross sectional area of the piston or second extruder extrusion channel should be kept as as small as possible to minimize the required force.

(f) Kinematics of 3D-Micro-Patterning

Figure 10:
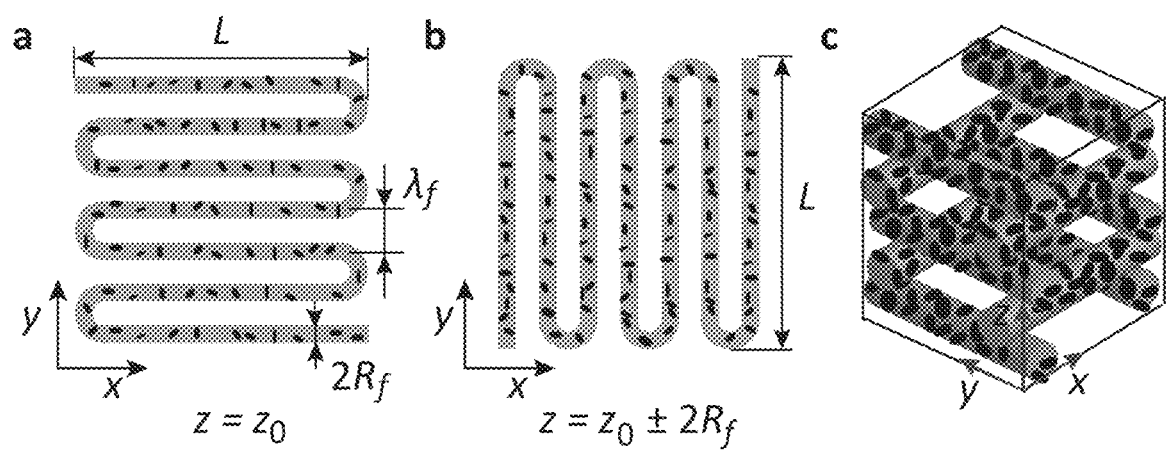
FIG. 10 illustrates a non-limiting microstructure of fibrous dosage forms herein (e.g., a cross-ply structure): (a) top view of the fibers in the plane $z=z_0$, (b) top view of the fibers in the plane $z=z_0 \pm 2R_f$, and (c) isometric view of the microstructure.
Figure 11:
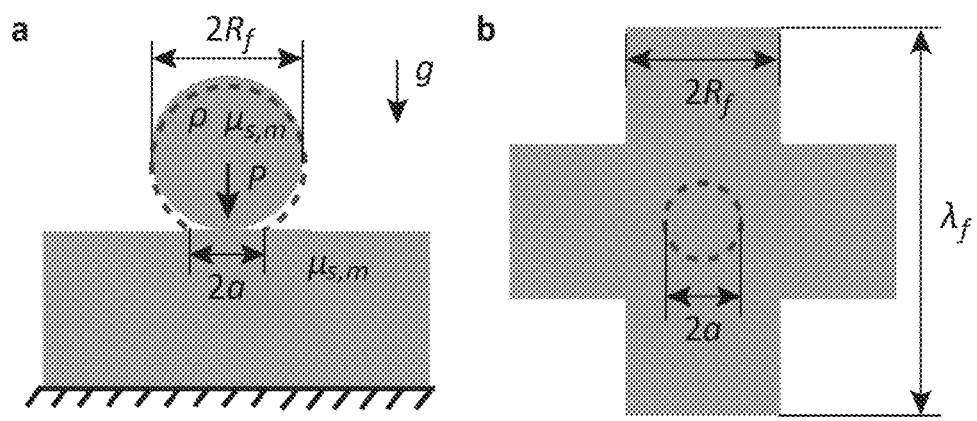
FIG. 11 is a non-limiting schematic illustrating contact deformation of fibers during or after micropatterning: (a) front view of deformation at the contact of crossed fibers, and (b) top view.

The extruded fiber may be deposited on a stage (e.g., micro-patterned) in a cross-ply arrangement as shown in FIGS. 10a-c. The time to micro-pattern, $t_m$, may be approximated as the ratio of the length of the plasticized fiber in the micro-patterned structure, $L_p$, and the stage or stream velocity, $v_{st}$:

$$t_m = \frac{L_p}{v_{st}} \quad (9)$$

where $$L_p = n_{fl} \times \left(\frac{L^2}{\lambda_f} + 2L\right) \quad (10)$$

Here $n_{fl}$ is the number of fibrous layers in the dosage form (along the z-axis), L the side length of a patterned (square) layer, and $\lambda_f$ the inter-fiber spacing in a layer.

(g) Bonding the Patterned Fibers

To ensure that the final dosage form is sufficiently strong, the deposited fibers may bond to the fibers below and above by viscous deformation and inter-diffusion of molecules. However, if the fibers deform too much and merge before they are dried, the fibrous pattern is lost.

Following the prior work (see, e.g., the U.S. application Ser. No. 15/964,058 titled "Method and apparatus for the manufacture of fibrous dosage forms"), under the highly approximate assumptions that (a) the plasticized fibers are Newtonian viscous, (b) adhesion due to the decreasing surface energy when the two surfaces contact is negligible, and (c) the deformations are small, the radius of the contact, a, may be expressed as:

$$a^3 = \int_0^t \frac{3PR_f}{8\mu_{s,m}} dt \quad (11)$$

where P is the contact load, $R_f$ the fiber radius, $\mu_{s,m}$ the "average" viscosity of the plasticized fibers, and t the time after initiation of the contact.

The load per contact may be the weight of the fibers of length, $\lambda_f$, above the plasticized contact, and may be written as:

$$P = \pi R_f^2 \lambda_f \rho g n_f \quad (12)$$

where $\rho$ is the density of the plasticized fiber, $n_f$ the number of fibers above the plasticized contact, and g the acceleration due to gravity.

Combining Eqs. (11) and (12) gives:

$$\frac{a}{R_f} = \left(\frac{3\pi\rho g \lambda_f n_f t}{8\mu_{s,m}}\right)^{1/3} \quad (13)$$

Using $\rho = 1100$ kg/m$^3$, $\lambda_f = 500$ µm, $n_f = 3$, and $\mu_{s,m} = 1000$ Pa·s, by Eq. (16) $a/R_f = 0.38$ after 20 seconds.

At the contact, moreover, the polymer molecules inter-diffuse across the contact interface, FIG. 9. The mean square displacement of a molecule, $\Delta x$, may be related to its diffusivity, D, and time, t, as:

$$\langle \Delta x^2(t) \rangle = 2Dt \quad (14)$$

Prior work suggests that the contact region approaches the bulk material if the mean square displacement of the molecules is of the order of their radius of gyration, $R_g$ (for further details, see, e.g., K. Jud, H. H. Kausch, J. G. Williams, Journal of Materials Science 16 (1981) 204-210). Thus the time to bond the contact surface by diffusion, $t_d$, may be estimated, roughly, by:

$$t_d \sim \frac{R_g^2}{2D} \quad (15)$$

Using $R_g \sim 5$ nm and $D \sim 10^{-11}$ m$^2$/s (as in a dilute solution), the bonding time by diffusion is only about a microsecond. In reality the bonding time may be slower because the paste may not quite be a dilute solution and the diffusivity of the polymer molecules may be smaller. Nevertheless, bonding may be quite fast after the two surfaces contact.

It is noted, again that any models and examples presented herein are non-limiting and for illustrative purposes only. More models and examples would be obvious to a person of ordinary skill in the art. All of them are within the spirit and scope of this invention.

Elements of the Method and Apparatus

In view of the non-limiting examples and theoretical models above, which are suggestive and approximate rather than exact, and other considerations, the method and apparatus disclosed herein may further comprise one or a combination of the following embodiments.

Generally, an active ingredient or an excipient may be injected into the extrusion channel as a solid material (e.g., a granular solid, filament, rod, etc), as a liquid material, as a plasticized material, as dissolved molecules in a liquid solvent, and so on.

Thus, in some embodiments, any apparatus disclosed herein may comprise one or more solids feeding units for injecting one or more solid constituents (e.g., one or more excipients and/or one or more drugs) into a first extruder extrusion channel. By way of example but not by way of limitation, a solids feeding unit may comprise a device that is capable of controlling the rate at which a solid constituent is injected into the extrusion channel, such as one or more rotating screws inside a barrel or powder feeding channel, at least one translating piston inside a barrel or powder feeding channel, and so on. The injection rate may, for example, be controlled volumetrically or gravimetrically. A solids feeding unit may operate in a continuous (e.g., a solid constituent is continuously injected into the extrusion channel), semi-continuous, or batch mode (e.g., specific volumes or masses of a solid constituent are injected into the extrusion channel at specific times and at specific rates). Any more examples of solids feeding units, or how solids feeding units may be operated, would be obvious to a person of ordinary skill in the art. All of them are within the scope of this invention.

In some embodiments, at least one input constituent is solid but plasticizes by solvation upon contact with a suitable solvent. The term "input constituent is generally referred to herein as an excipient, and in some cases also as a drug, that is injected into the extrusion channel. Furthermore, the terms "plasticize" or "plasticizing" and "fluidize" or "fluidizing" are used interchangeably herein. Moreover, in the context herein a solid constituent that plasticizes by solvation upon contact with a suitable solvent (e.g., a solid constituent that solvates upon contact with a suitable solvent) is referred to as a solid constituent having a viscosity that decreases upon contact with a suitable solvent. Typically, a solid constituent may be considered plasticized as soon as its viscosity has decreased so much that it is of the order of or smaller than the viscosity of a plasticized matrix.

Thus, to form a plasticized matrix by solvating at least one injected solid constituent, the apparatus disclosed herein may further comprise at least one liquid or solvent feeding unit attached to a feeding port for injecting solvent into the extrusion channel A solvent feeding unit comprises any device to move/dispense/inject solvent at a controlled rate into the extrusion channel, such as a peristaltic pump, a diaphragm pump, a rotary vane pump, a syringe pump, or any other rotary or positive displacement pump, among others. Any more examples of liquid or solvent feeding units would be obvious to a person of ordinary skill in the art. All of them are within the scope of this invention.

Also, in some embodiments at least one input constituent is solid but plasticizes by melting upon heating. In the context of the invention herein a solid constituent that plasticizes by melting upon heating is referred to a solid constituent (e.g., an excipient or an active ingredient) having a viscosity that decreases upon increasing the temperature. Typically, a solid constituent may be considered plasticized as soon as its viscosity has decreased so much that it is of the order of or smaller than the viscosity of a plasticized matrix. Thus, the melting temperature of a solid constituent in the invention herein is referred to the temperature at which the viscosity of said solid constituent has decreased so much upon heating that it is of the order of or smaller than the viscosity of a plasticized matrix. A solid constituent that plasticizes by melting upon heating is preferably chemically stable at elevated temperatures (e.g., at the temperature above the melting temperature of said constituent).

Thus, for fluidizing (or plasticizing) at least one injected solid constituent, or for preventing solidification of one or more fluidized or plasticized constituents, the apparatus herein may further comprise at least one heating element. Said at least one heating element may, for example, be wrapped around an extrusion channel or a fraction thereof. In the context of this disclosure, all such heating (or cooling) elements that are partially wrapped around an extrusion channel or the extrusion channel walls are considered "wrapped around the extrusion channel". Non-limiting examples of heating elements that are wrapped around an extrusion channel comprise band heaters, coil heaters, etc.

In some embodiments, at least one heating element may be fully or partially embedded into the walls of an extrusion channel. In the context of this disclosure, all such heating (or cooling) elements that are "fully or partially embedded into the walls of an extrusion channel" are considered "embedded into the housing". Thus, non-limiting examples of heaters that are embedded into the walls of an extrusion channel include cartridge heaters that may be fixed in and surrounded by the walls of an extrusion channel, fluid channels in the walls of an extrusion channel that are filled with a circulating temperature-controlled fluid, etc. It may be noted that a fluid that circulates through channels of the walls of an extrusion channel may not only allow to heat the walls of an extrusion channel or a fraction thereof, but may also allow to cool them. The temperature of the circulating fluid should be lower than the temperature of the walls of an extrusion channel (or a fraction thereof) in this case. Any more examples of heating elements or examples of how the heating of the walls of an extrusion channel or an input constituent may be performed would be obvious to a person of ordinary skill in the art. All of them are within the scope of this invention.

In some embodiments, a fraction of (or all) the input material (e.g., drug, excipient, solvent, etc.) is supplied to a first extruder's extrusion channel in the form of a plasticized matrix. Thus, any apparatus or method disclosed herein may comprise at least one plasticized matrix feeding unit for feeding or injecting a plasticized matrix into the extrusion channel By way of example but not by way of limitation, said plasticized matrix feeding unit may comprise a device that is capable of controlling the rate at which a plasticized matrix is injected into the extrusion channel, such as one or more rotating screws inside a barrel, at least one translating piston inside a barrel, a peristaltic pump, and so on. The injection rate may, for example, be controlled volumetrically or gravimetrically. Also a plasticized matrix feeding unit may be operated in a continuous (e.g., a plasticized matrix is continuously injected into the extrusion channel), semi-continuous, or batch mode (e.g., specific volumes of a plasticized matrix are injected into the extrusion channel at specific times and at specific rates). Any more examples of plasticized matrix feeding units, or how plasticized matrix feeding units may be operated, would be obvious to a person of ordinary skill in the art. All of them are within the scope of this invention.

It may be noted, moreover, that in any aspect of the invention herein, a first extruder extrusion channel may have one or multiple feeding ports for injecting solid material, liquid material, plasticized material, and so on into the first extruder extrusion channel.

As mentioned in the description of the non-limiting aspects of the disclosed apparatus and method, the apparatus or method herein generally comprises means for forming and extruding a plasticized matrix in the first extruder's extrusion channel. In the invention herein, the term "means for forming and extruding plasticized matrix" generally comprises a device for applying mechanical work on a solid (e.g., a granular solid, filament, sheet, etc.) or a fluid (e.g., a plasticized matrix, liquid, etc.) to transport said solid or fluid towards an exit port of an extrusion channel A non-limiting example of a means for forming and extruding plasticized matrix is a screw. A screw may, for example, comprise multiple sections with different geometries for performing specific functions or steps (e.g., transporting a granular solid towards an exit port, transporting a plasticized matrix towards an exit port, mixing drug and excipient, mixing excipient and solvent, and so on). Furthermore, a screw may perform specific functions or steps concurrently. Thus, a screw allows to integrate multiple functions or steps into a continuous, steady process. A screw may operate as 'single screw' or within an arrangment of multiple screws, such as a 'twin screw'. Other non-limiting examples of means for forming and extruding plasticized matrix include fluid pumps (e.g., extrusion gear pumps, melt pumps, peristaltic pumps, diaphragm pumps, rotary vane pumps, etc.), pistons, and so on. Any means for forming and extruding plasticized matrix may be operated with at least one motor (e.g., an electrical AC motor, DC motor, stepper motor, servo motor, etc.), or with at least one hydraulic actuator, or with at least one pneumatic actuator, among others. Any more examples of means for forming and extruding plasticized matrix would be obvious to a person of ordinary skill in the art. All of them are within the scope of this invention.

Moreover, an apparatus or method as disclosed herein generally comprises at least a valve (e.g., a first valve) at a first extruder's exit port. Said valve may permit flow from the first extruder extrusion channel into the second extruder extrusion channel Said valve may, however, restrict or block flow from the second extruder extrusion channel into the first extruder extrusion channel. Moreover, a valve, or first valve, may allow flow of plasticized matrix from a first extruder extrusion channel through an exit port of said first extruder extrusion channel and into the channel of a second extruder while a piston of said second extruder recedes and/or while said second extruder extrusion channel is filled with plasticized matrix from said first extruder extrusion channel A valve, or first valve, may further block flow of plasticized matrix from the channel of a second extruder through a first extruder's exit port while a piston of said second extruder advances and/or while plasticized fiber is extruded through a fiber fabrication exit port of said second extruder extrusion channel.

In some embodiments, said valve or "first valve" comprises a check valve. A check valve may, for example, be a passive valve. A "passive valve" is understood herein as a valve that does not comprise an actuator (e.g., a passive valve is a valve that does not require an actuator or extrernal actuation to be functional or execute the required functions). By way of example but not by way of limitation, a check valve (e.g., a passive check valve) at a first extruder's exit port may be open and permit flow through it while plasticized matrix from a first extruder extrusion channel is extruded into a second extruder extrusion channel. The check valve may be closed, however, and block flow from the second extruder extrusion channel into the first extruder extrusion channel while plasticized matrix is extruded from the second extruder extrusion channel through a fiber fabrication exit port. Thus, a check valve may only allow flow of plasticized matrix in one way or direction. Plasticized matrix that has been extruded from a first extruder extrusion channel to a second extruder extrusion channel may be prevented from returning into the first extruder extrusion channel Such check valves may also be referred to as "one-way valves" or "non-return" valves.

In a check valve, however, switching from an "open" state to a "closed" state upon changing the flow direction may not be immediate. Thus, in some cases, some plasticized matrix may leak from a second extruder extrusion channel into a first extruder extrusion channel as the flow direction of plasticized matrix is changed from filling a second extruder extrusion channel to extruding plasticized matrix out of said second extruder extrusion channel.

Leakage can be reduced or minimized, however, if the check valve comprises a "cracking pressure" or "opening pressure". A cracking pressure is the minimum pressure required to "open" a check valve and have fluid flowing through said check valve in the direction said check valve allows flow. Thus, a cracking pressure is also referred to herein as "opening pressure". In some embodiments, to prevent leakage through a check valve upon switching the flow direction of plasticized matrix (e.g. to prevent backflow from a second extruder extruder channel into a first extruder extrusion channel), a check valve comprises a cracking pressure greater than 0.01 MPa. This includes, but is not limited to a cracking pressure greater than 0.02 MPa, or greater than 0.05 MPa or greater than 0.1 MPa, or greater than 0.2 MPa, or greater than 0.5 MPa, or greater than 1 MPa. Preferably, a cracking pressure of a check valve should be greater than at least 0.1 MPa.

To prevent excessive pressure buildup in the first extruder extrusion channel, however, the cracking pressure should also not be too large. Thus, in some embodiments, the cracking pressure of a check valve at a first extruder extrusion channel exit port is no greater than 10,000 MPa. This includes, but is not limited to a cracking pressure of a check valve at a first extruder extrusion channel exit port no greater than 5,000 MPa, or no greater than 2,000 MPa, or no greater than 1,000 MPa, or no greater than 800 MPa, or no greater than 600 MPa, or no greater than 500 MPa, or no greater than 400 MPa, or no greater than 300 MPa, or no greater than 200 MPa, or no greater than 100 MPa.

In some embodiments, moreover, a valve at an exit port of a first extruder extrusion channel comprises a "three-way valve". A three-way valve generally is an active valve, which requires actuation to switch from one flow path to another. By way of example but by way of limitation, a three-way valve may be actuated by a pneumatic actuator or by an electric actuator (e.g., a solenoid actuator, etc.) to switch from one flow path to another.

Said three-way valve may comprise a flow path allowing flow from a first extruder extrusion channel through an exit port of said first extruder extrusion channel into the channel of a second extruder, while blocking or restricting flow from said first extruder extrusion channel to a fiber fabrication exit port end of said second extruder extrusion channel Said three-way valve may further comprise a flow path allowing flow through a second extruder extrusion channel and through a fiber fabrication exit port of said second extruder extrusion channel, while blocking or restricting flow from said second extruder extrusion channel into an extrusion channel of a first extruder.

In some embodiments, a second extruder extrusion channel comprises at least a second valve. Said second valve may for example, be positioned between an input port and a fiber fabrication exit port of said second extruder extrusion channel Said second valve may restrict flow through said fiber fabrication exit port while the second extruder extrusion channel is filled with plasticized matrix. Said second valve may further permit flow through said fiber fabrication exit port while a piston advances to extrude plasticized fiber through said fiber fabrication exit port.

Similarly, while plasticized matrix is extruded from the first extruder extrusion channel into a second extruder extrusion channel, the flow of plasticized matrix through a fiber fabrication exit port may be blocked or prevented by a movable solid surface. Said movable solid surface may be removably attached or pressed to said fiber fabrication exit port to flexibly block flow of plasticized matrix through said fiber fabrication exit port.

Moreover, in some embodiments, the movable solid surface may be attached to or included in the movable stage. Such embodiments can be preferrable because no additional actuators are required.

To prevent wear of the fiber fabrication exit port channel by the removably attached solid surface, and for other reasons, in some embodiments, said movable solid surface may comprise a solid composition or solid matter with a stiffness or elastic modulus smaller than the stiffness or elastic modulus of the fiber fabrication exit port channel. In some embodiments, moreover, to ensure that the movable solid surface tighly seals the fiber fabrication exit port, and for other reasons, the movable solid surface is compliant.

Non-limiting examples of materials which the composition of the movable solid surface may include comprise polymers, such as polyethylene, polypropylene, polycarbonate, polytetrafluoroethylene, polyvinylfluoride, fluorinated ethylene-propylene, perfluoroalkoxy polymer, polyvinylidene fluoride, and so on. Generally, however, due to their high resistance to chemical degradation, and for other reasons, such fluoropolymers as polytetrafluoroethylene, polyvinylfluoride, fluorinated ethylene-propylene, perfluoroalkoxy polymer, polyvinylidene fluoride, and so on may be preferred for inclusion in the composition of a movable solid surface.

Figure 12:
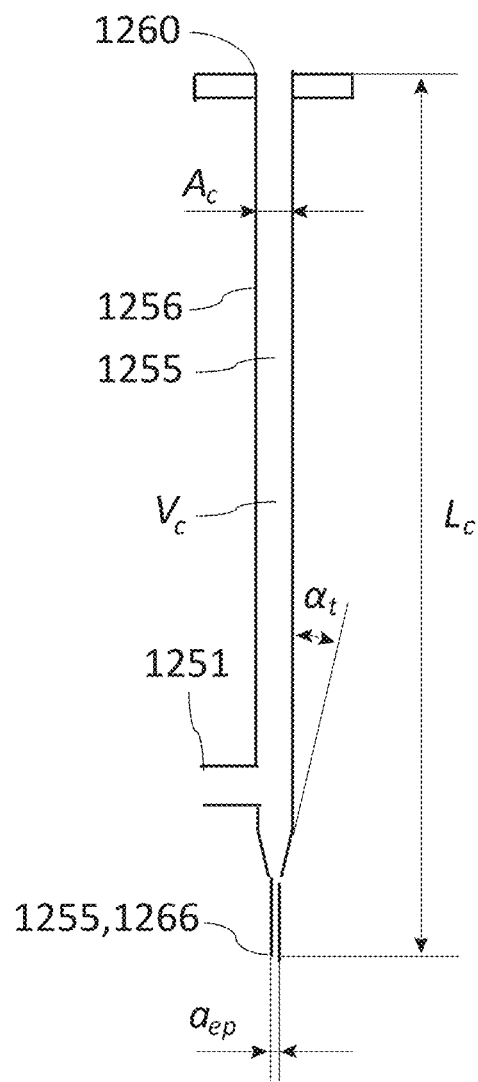
FIG. 12 presents a non-limiting schematic of a second extruder extrusion channel according to the invention herein.

FIG. 12 presents a non-limiting example of a second extruder extrusion channel 1255. The channel 1255 is bound by channel walls 1256, an input port 1251, a first end 1260, and a second end 1255 comprising a fiber fabrication exit port 1266. The channel 1255 comprises a volume, $V_c$, a cross sectional area, $A_c$, and a length, $L_c$. The channel 1255 further tapers down before a fiber fabrication exit port 1266 at a taper angle, $\alpha_c$. The channel 1255 further comprises a cross sectional area of the fiber fabrication exit port, $a_{ep}$.

The volume, $V_c$ of a second extruder extrusion channel should generally be large enough to ensure that a sufficient amount of fiber can be deposited during a channel filling-micropatterning cycle. Thus, in some embodiments, the volume of a second extruder extrusion channel is greater than 0.05 cm$^3$. This includes, but is not limited to a volume of a second extruder extrusion channel greater than 0.01 cm$^3$, or greater than 0.02 cm$^3$, or greater than 0.05 cm$^3$, or greater than 0.1 cm$^3$, or greater than 0.2 cm$^3$, or greater than 0.5 cm$^3$, or greater than 1 cm$^3$, or greater than 1.5 cm$^3$. or in the ranges 0.2 cm$^3$-25 cm$^3$, 0.5 cm$^3$-20 cm$^3$, 0.5 cm$^3$-15 cm$^3$.

The volume, $V_c$, of a second extruder extrusion channel, however, typically should also not be too large to assure that the flow rate or speed of extruded fiber can be precisely controlled by an advancing piston, and for other reasons. Thus, in some embodiments, a second extruder extrusion channel comprises a volume no greater than 100 cm$^3$. This includes, but is not limited to a volume of a second extruder extrusion channel no greater than 75 cm$^3$, or no greater than 50 cm$^3$, or no greater than 30 cm$^3$, or no greater than 20 cm$^3$.

A cross sectional area, $A_c$, of a second extruder extrusion channel should generally not be too large to assure that the force acting on the piston extruding plasticized fiber through a fiber fabrication exit port of said second extruder extrusion channel is not too large. In some embodiments, therefore, a cross sectional area of a second extruder extrusion channel is no greater than 100 cm$^2$. This includes, but is not limited to a cross sectional area of a second extruder extrusion channel no greater than 75 cm$^2$, or no greater than 50 cm$^2$, or no greater than 30 cm$^2$, or no greater than 20 cm$^2$, or no greater than 10 cm$^2$, or no greater than 5 cm$^2$, or no greater than 2 cm$^2$.

A cross sectional area, $A_c$, of a second extruder extrusion channel, however, generally should also be large enough to ensure that the volume, $V_c$, of the extruder channel is large enough so that a sufficient amount of fiber can be deposited during a channel filling-micropatterning cycle. In some embodiments, therefore, a cross sectional area of a second extruder extrusion channel is greater than 0.001 cm$^2$. This includes, but is not limited to a cross sectional area of a second extruder extrusion channel greater than 0.002 cm$^2$, or greater than 0.005 cm$^2$, or greater than 0.01 cm$^2$, or greater than 0.02 cm$^2$.

In some embodiments, moreover, a second extruder extrusion channel comprises a length, $L_c$, in the range 0.5 cm-100 cm. This includes, but is not limited to a length of a second extruder extrusion channel in the ranges 1 cm-100 cm, or 2 cm-80 cm, or 3 cm-80 cm, or 4 cm-80 cm, or 4 cm-50 cm, or 5 cm-100 cm, or 5 cm-50 cm, or 5 cm-30 cm.

In some embodiments, furthermore, a second extruder extrusion channel comprises a channel that is substantially straight along its longitudinal axis. In some embodiments, moreover, a second extruder extrusion channel comprises a section or segment of substantially uniform or constant cross sectional area or diameter. In some embodiments, furthermore, a second extruder extrusion channel is substantially circular along its longitudinal axis.

In some embodiments, moreover, a second extruder extrusion channel cross section tapers down before a fiber fabrication exit port. In some embodiments, moreover, a second extruder extrusion channel cross section tapers down before a fiber fabrication exit port to the cross section of said exit port. In some embodiments, to minimize the pressure drop across a taper or across a contraction while extruding plasticized matrix through said taper or said contraction, the angle of a taper, $\alpha_c$, is no greater than 70 degrees. This includes, but is not limited to an angle of a taper no greater than 60 degrees, or no greater than 50 degrees, or no greater than 40 degrees, or no greater than 35 degrees, or no greater than 30 degrees.

In some embodiments herein, a fraction of the channel walls of a second extruder extrusion channel comprises a composition that includes at least a glass. A non-limiting example of a glass includes borosilicate.

In some embodiments, moreover, a composition of a second extruder extrusion channel wall comprises a metal. In some embodiments, moreover, a composition of a second extruder extrusion channel wall at a fiber fabrication exit port comprises a metal. A non-limiting example of a preferred metal is stainless steel.

Figure 13:
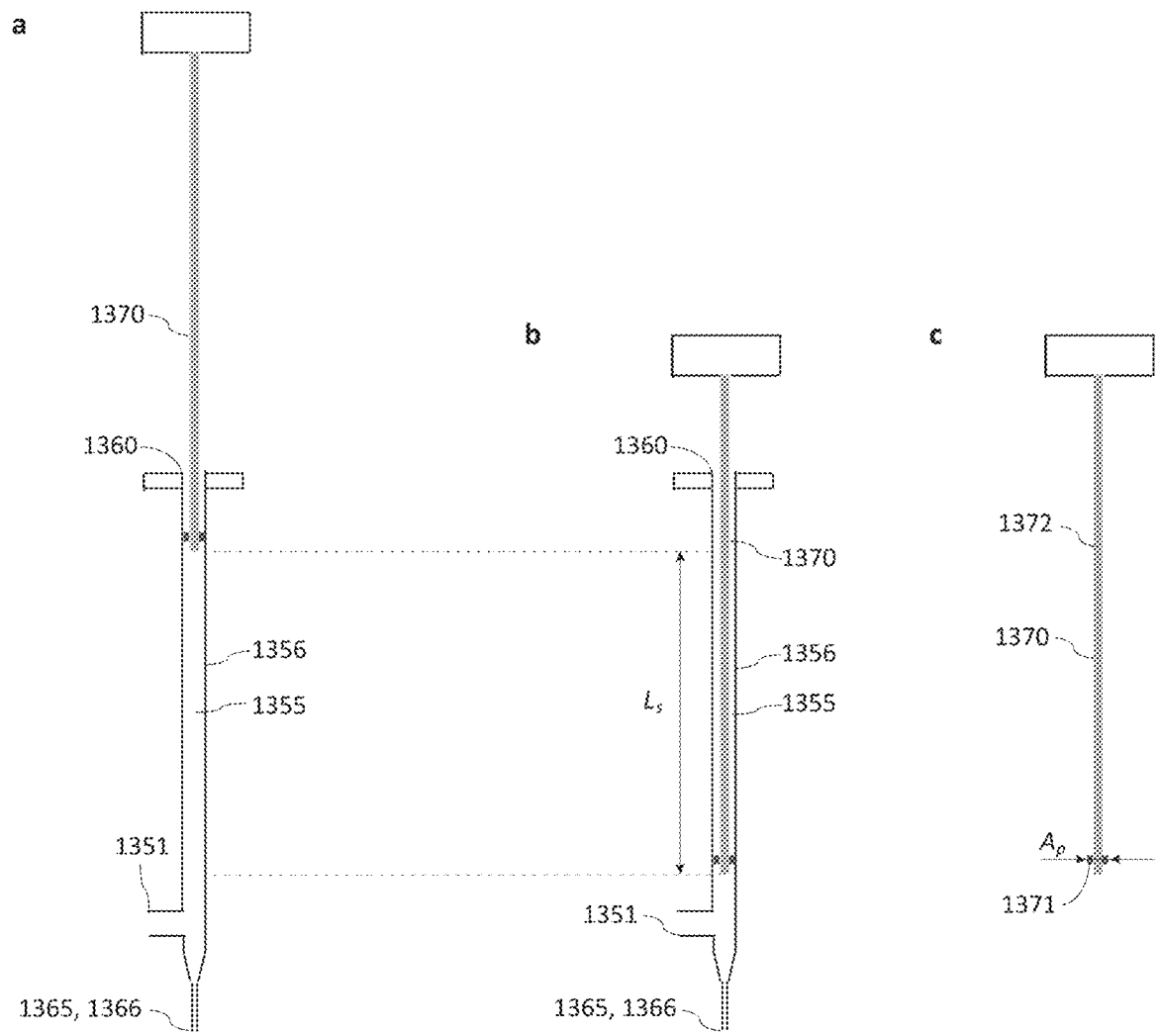
FIG. 13 shows non-limiting schematics of a second extruder extrusion channel and a piston in contact with and enclosed by the channel walls of said second extruder extrusion channel.

FIG. 13 presents non-limiting schematics of a second extruder extrusion channel 1355 and a piston 1370 in contact with and enclosed by the channel walls 1356 of said second extruder extrusion channel 1355. The extrusion channel 1355 is bound by channel walls 1356, an input port 1351, a first end 1360, and a second end 1365 comprising a fiber fabrication exit port 1366. FIG. 13*a* presents a non-limiting schematic of said second extruder extrusion channel 1355 and said piston 1370 in a receded or fully receded position. The piston 1370 is translatable along the channel's 1355 longitudinal axis between said first 1360 and second ends 1365. (It may be noted that in some preferred embodiments, a piston 1370 is translatable along the channel's 1355 longitudinal axis between said first end 1360 and said input port 1351.) FIG. 13*b* presents a non-limiting schematic of said second extruder extrusion channel 1355 and said piston 1370 in an advanced or fully advanced position.

In some embodiments, the piston in contact with the second extruder extrusion channel comprises a cross sectional area no greater than 100 cm$^2$. This includes, but is not limited to a cross sectional area of a second extruder extrusion channel no greater than 75 cm$^2$, or no greater than 50 cm$^2$, or no greater than 30 cm$^2$, or no greater than 20 cm$^2$, or no greater than 10 cm$^2$, or no greater than 5 cm$^2$, or no greater than 2 cm$^2$.

In some embodiments, the stroke length, $L_s$, of a piston is in the range 0.5 cm-100 cm. This includes, but is not limited to a stroke length of a piston in the ranges 1 cm-100 cm, or 2 cm-80 cm, or 3 cm-80 cm, or 4 cm-80 cm, or 4 cm-50 cm, or 5 cm-100 cm, or 5 cm-50 cm, or 5 cm-30 cm.

In some embodiments, the stroke volume of the piston (e.g., the maximum volume displaced by the piston in the second extruder extrusion channel) is in the range 0.2 cm$^3$-25 cm$^3$. This includes, but is not limited to a stroke volume of the piston in a second extruder extrusion channel in the ranges 0.5 cm$^3$-20 cm$^3$, 0.5 cm$^3$-15 cm$^3$.

Moreover, to prevent, block, or restrict flow of plasticized matrix through the first end of the extrusion channel (e.g., to prevent flow of plasticized matrix between the piston and the extrusion channel), said piston comprises a seal around its circumference. FIG. 13*c* schematically illustrates said non-limiting piston without extrusion channel. The non-limiting piston comprises a rod and a seal. By way of example but not by way of limitation, said seal may comprise one or more rings, one or more sleeves (e.g., one or more rings or one or more sleeves around the piston rod), etc. In some embodiments, the seal of said piston comprises a composition that is softer than the composition of the extruder channel channel walls. This includes, but is not limited to a seal composition with a stiffness or elastic modulus smaller or substantially smaller than the stiffness or elastic modulus of the second extruder channel walls.

Non-limiting examples of materials which the composition of a piston seal may include comprise polymers, such as polyethylene, polypropylene, polycarbonate, polytetrafluoroethylene, polyvinylfluoride, fluorinated ethylene-propylene, perfluoroalkoxy polymer, polyvinylidene fluoride, and so on. Generally, however, due to their high resistance to chemical and thermal degradation, and for other reasons, such fluoropolymers as polytetrafluoroethylene, polyvinylfluoride, fluorinated ethylene-propylene, perfluoroalkoxy polymer, polyvinylidene fluoride, and so on may be preferred for inclusion in the composition of a piston seal.

In some embodiments, moreover, a piston is operated or driven by an electric motor capable of slowly advancing the piston at a controlled speed for extruding fiber at a controlled (e.g., precisely controlled) speed through and out of a fiber fabrication exit port. In some embodiments, the piston advances at a speed no greater than 20 mm/s to extrude fiber through a fiber fabrication exit port. This includes, but is not limited to a piston advancing at a speed no greater than 10 mm/s, or no greater than 5 mm/s, or no greater than 2 mm/s, or no greater than 1 mm/s to extrude fiber through a fiber fabrication exit port.

In some embodiments, the piston and the motor to actuate said piston are designed to extrude plasticized matrix or fiber through a fiber fabrication exit port at a flow rate (e.g. at a precisely controlled flow rate) in the range of $1\times10^{-4}$ mm$^3$/s-$5\times10^3$ mm$^3$/s. This includes, but is not limited to the piston and the motor to actuate said piston designed to extrude plasticized matrix or fiber through a fiber fabrication exit port at a flow rate in the ranges of $2\times10^{-4}$ mm$^3$/s-$5\times10^3$ mm$^3$/s, $5\times10^{-4}$ mm$^3$/s-$5\times10^3$ mm$^3$/s, $10\times10^{-4}$ mm$^3$/s-$5\times10^3$ mm$^3$/s, $1\times10^{-4}$ mm$^3$/s-$2\times10^3$ mm$^3$/s, or $2\times10^{-4}$ mm$^3$/s-$2\times10^3$ mm$^3$/s. In other words, while the piston is advancing the piston and the motor to actuate said piston may be capable of reducing the volume of plasticized matrix in a second extruder extrusion channel at a rate in the range of $1\times10^4$ mm$^3$/s-$5\times10^3$ mm$^3$/s (e.g., $2\times10^4$ mm$^3$/s-$5\times10^3$ mm$^3$/s, $5\times10^4$ mm$^3$/s-$5\times10^3$ mm$^3$/s, $10\times10^4$ mm$^3$/s-$5\times10^3$ mm$^3$/s, $1\times10^4$ mm$^3$/s-$2\times10^3$ mm$^3$/s, or $2\times10^4$ mm$^3$/s-$2\times10^3$ mm$^3$/s).

Therefore, in some embodiments the rate at which the piston displaces volume as it advances towards a fiber fabrication exit port is in the range of $1\times10^4$ mm$^3$/s-$5\times10^3$ mm$^3$/s. This includes, but is not limited to a rate at which the piston displaces volume as it advances towards a fiber fabrication exit port in the ranges of $2\times10^4$ mm$^3$/s-$5\times10^3$ mm$^3$/s, $5\times10^4$ mm$^3$/s-$5\times10^3$ mm$^3$/s, $10\times10^4$ mm$^3$/s-$5\times10^3$ mm$^3$/s, $1\times10^4$ mm$^3$/s-$2\times10^3$ mm$^3$/s, or $2\times10^4$ mm$^3$/s-$2\times10^3$ mm$^3$/s.

Figure 14:
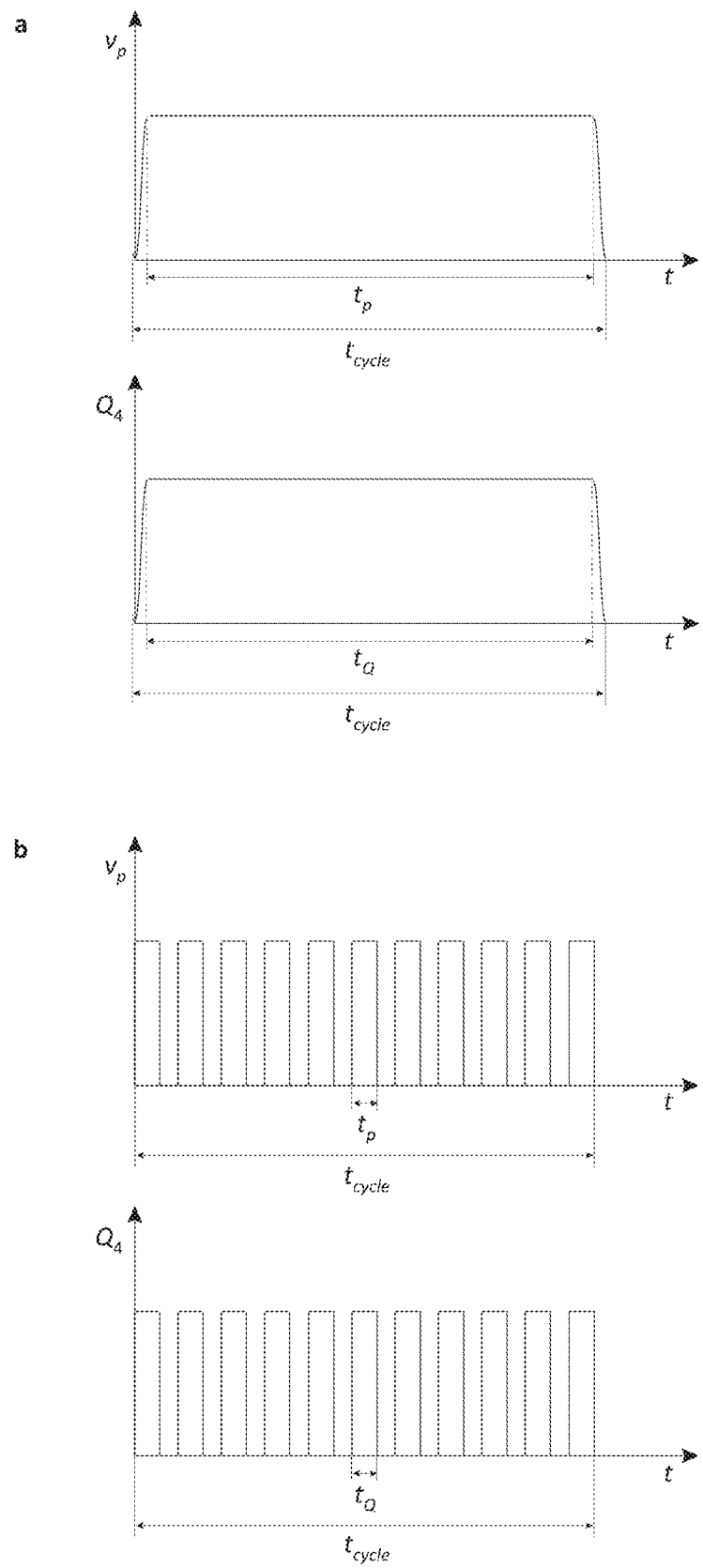
FIG. 14 schematically shows non-limiting plots of piston velocity and flow rate of extruded fiber versus time during a fiber deposition cycle.

As shown schematically in the non-limiting FIG. 14, in some embodiments a piston advances at a constant or at a substantially constant speed while extruding fiber through a fiber fabrication exit port. This includes, but is not limited to a piston advancing at a constant or at a substantially constant speed from the time point when the corresponding second extruder extrusion channel is filled, and the piston starts to advance, to the time point when the corresponding second extruder extrusion channel is substantially empty, and may need to be refilled with plasticized matrix from the first extruder, FIG. 14a. The cycle between the time point when a second extruder extrusion channel is filled and the piston starts to advance to the time point when said second extruder extrusion channel is substantially empty, and may need to be refilled with plasticized matrix from the first extruder, is also referred to herein as "fiber deposition cycle". The time or the "cycle time" of a fiber deposition cycle is also referred to as "$t_{cycle}$". In other non-limiting examples, as illustrated schematically in FIG. 14b, a piston may advance at a constant or at a substantially constant speed during specific time periods within a fiber deposition cycle.

In some embodiments, therefore, the flow rate of plasticized fiber through a fiber fabrication exit port and the rate at which plasticized fiber is deposited on a movable stage is constant or substantially constant while fiber is extruded through a fiber fabrication exit port. In some embodiments, moreover, the flow rate of plasticized fiber through a fiber fabrication exit port and the rate at which plasticized fiber is deposited on a movable stage is constant or substantially constant during a time period (e.g., a time length or a time portion or a time section) smaller than the fiber deposition cycle. In some embodiments, moreover, a fiber deposition cycle comprises time periods where fiber is extruded through a fiber fabrication exit port and time periods where no fiber is extruded through said fiber fabrication exit port. Any more examples of the speed of an advancing piston versus time or the speed of an extruded plasticized fiber versus time would be obvious to a person of ordinary skill in the art. All of them are within the scope of this invention.

In some embodiments, moreover, at least one fiber fabrication exit port is designed to extrude fibrous extrudate with a fiber thickness less than 2.5 mm. This includes, but is not limited to at least one fiber fabrication exit port designed to extrude fibrous extrudate with thickness less than 2.25 mm, or less than 2 mm, or less than 1.75 mm, or less than 1.5 mm, or less than 1.25 mm, or less than 1 mm, or in the ranges 1 µm-2 mm, or 2 µm-2 mm, or 2.5 µm-2 mm, or 5 µm-2 mm, or 10 µm-2 mm, or 5 µm-1.5 mm, or 10 µm-1.5 mm, or 10 µm-1.25 mm, or 20 µm-1.5 mm, or 20 µm-1.25 mm.

In some embodiments, furthermore, the stage on which one or more fibers may be deposited comprises a solid plate or a solid build platform. Generally, said solid plate or solid build platform or "stage" is translatable in at least two directions relative to a fiber fabrication exit port for depositing one or more plasticized fibers along a path defined by motion of said stage. In some embodiments, moreover, a stage is rotatable relative to one or more exit ports for depositing one or more plasticized fibers along a path defined by motion of said stage. Preferably, a stage is movable in at least three directions (e.g., in an x-direction, in a y-direction, and in a z-direction) relative to at least one fiber fabrication exit port for depositing one or more plasticized fibers along a path defined by the motion of said stage.

Thus, generally, the term "translating or rotating stage" is understood herein as a stage that can be moved (e.g. a stage that can translate or rotate, or a stage that has the capacity or the ability to translate or rotate) with respect to an exit port. This includes, but is not limited to a stage that can be moved and an exit port that is not movable (e.g., an exit port that is fixed in space), or an exit port that is movable and a stage that is not movable, or an exit port that is movable and a stage that is movable. Typically, however, the fiber fabrication exit port, extrusion channel, etc. are fixed or nonmovable in space, and the stage is movable or translatable in an x-direction, in a y-direction, and in a z-direction. It may be noted that the terms "stage", "x-y-z stage", "translating or rotating stage", and "translating stage" are generally used interchangeably in this disclosure.

To ensure that a plasticized fiber can be patterned along the desired path, and to ensure that said fiber bonds to a substrate or to deposited fibers or to a deposited structural framework, a plasticized fiber or a plasticized matrix may be moderately fluidic. Thus, in some embodiments a plasticized matrix or fiber comprises a shear viscosity no greater than 200,000 Pa·s at a shear rate no greater than 10/s. This includes, but is not limited to a plasticized matrix or fiber comprising a shear viscosity no greater than 100,000 Pa·s, or no greater than 75,000 Pa·s, or no greater than 50,000 Pa·s, or no greater than 20,000 Pa·s, or no greater than 10,000 Pa·s, or no greater than 7500 Pa·s, or no greater than 5000 Pa·s at a shear rate no greater than 10/s.

However, to adequately preserve the deposited three dimensional structural framework and to prevent or avoid that the deposited fibrous pattern is lost, the viscosity of a plasticized fiber or of a plasticized matrix should not be too small. In other words, a plasticized fiber should be viscous enough to ensure that a deposited fibrous pattern is preserved. Thus, in some embodiments the shear viscosity of a plasticized matrix or fiber is greater than 0.1 Pa·s at a shear rate no greater than 10/s. This includes, but is not limited to a shear viscosity of a plasticized matrix or fiber greater than 0.5 Pa·s, or greater than 1 Pa·s, or greater than 5 Pa·s, or greater than 10 Pa·s, or greater than 20 Pa·s, or greater than 50 Pa·s at a shear rate no greater than 10/s.

In some embodiments, the viscosity of an extruded, exiting plasticized fiber is in the range between 10 Pa·s and 100,000 Pa·s at a shear rate of 1/s. This includes, but is not limited to a viscosity of an extruded, exiting plasticized fiber is in the range between 50 Pa·s and 50,000 Pa·s at a shear rate of 1/s.

In some embodiments, the viscosity of a plasticized fiber is controlled by the weight fraction of solvent in said fiber. Thus, in some embodiments, the weight or volume fraction of solvent in a plasticized fiber is greater than 0.1. This includes, but is not limited to a weight or volume fraction of solvent in a plasticized fiber greater than 0.125, or greater than 0.15, or greater than 0.2. In some embodiments, moreover the weight or volume fraction of solvent in a plasticized fiber is no greater than 0.925. This includes, but is not limited to a weight or volume fraction of solvent in a plasticized fiber no greater than 0.9, or no greater than 0.85, or no greater than 0.8, or no greater than 0.75.

Moreover, for achieving or producing precisely controlled fibrous patterns, the speed or velocity of a stage or substrate with respect to a fiber fabrication exit port may generally be about the same as the speed or velocity of a fibrous extrudate effluent from said fiber fabrication exit port. In the specification herein, the term "substrate" is generally referred to as a surface on which fiber is patterned. Thus, in some embodiments the speed or velocity of a substrate or stage with respect to a fiber fabrication exit port, $v_{st}$, is in the range 0.1-10 times the speed or velocity of a fibrous extrudate, $v_f$. This includes, but is not limited to $v_{st}$ in the range 0.2-5 times $v_f$, or $v_{st}$ in the range 0.3-3 times $v_f$, or $v_{st}$ in the range 0.5-2 times $v_f$, or $v_{st}$ in the range 0.75-1.5 times $v_f$. It may be obvious to a person of ordinary skill in the art that the path and velocity of a substrate with respect to an exit port may be computer-controlled.

Moreover, for achieving precise control of the deposition location of an extruded plasticized fiber, in some embodiments the distance between a fiber fabrication exit port and the deposition location of a plasticized fiber effluent from said exit port is no greater than 7 mm while assembling said fiber to a three dimensional structural framework. This includes, but is not limited to a distance between a fiber fabrication exit port and the deposition location of a plasticized fiber effluent from said exit port no greater than 6 mm, or no greater than 5 mm, or no greater than 4 mm, or no greater than 3 mm, or no greater than 2 mm while assembling said fiber to a three dimensional structural framework.

Similarly, in some embodiments the distance between a fiber fabrication exit port and a deposition location of a plasticized fiber on a substrate or on a stage is no greater than ten times the thickness of said fiber while assembling said fiber to a three dimensional structural framework. This includes, but is not limited to a distance between a fiber fabrication exit port and a deposition location of a fiber on a substrate no greater than 9 times, or no greater than 8 times, or no greater than 7 times, or no greater than 6 times, or no greater than 5 times the thickness of said fiber while assembling said fiber to a three dimensional structural framework. It may be noted that the deposition location of a plasticized fiber can be the surface of a substrate (e.g., the top surface of an x-y-z stage, the top surface of a deposited structural framework, the top surface of a deposited fiber bed, the top surface of a deposited structure, etc.).

In some embodiments, an inter-fiber spacing, and/or a fiber thickness, etc. can be precisely (or deterministically) controlled in a fibrous dosage form prepared by the method or apparatus herein. In the context of this invention, a variable (or a parameter, e.g., an inter-fiber spacing or a fiber thickness) is precisely controlled if it is deterministic and not stochastic (or random). A variable or parameter may be deterministic if, upon multiple repetitions of a step that includes said variable, the standard deviation of the values of said variable is smaller than the average value. This includes, but is not limited to a standard deviation of the values of said variable smaller than half the average value, or smaller than one third of the average value, or smaller than a quarter of the average value, or smaller than one fifth of the average value, or smaller than one sixth of the average value, or smaller than one eight of the average value, or smaller than one tenth of the average value of said variable. By way of example but not by way of limitation, if a fiber is produced multiple times under identical conditions, the standard deviation of the thickness of said fibers is less than one tenth of the average value of said fibers' thickness. Similarly, if an inter-fiber spacing is produced multiple times under identical conditions, the standard deviation of said inter-fiber spacing may be less than one fifth of the average value of said inter-fiber spacing.

During or after patterning on a substrate, a plasticized fiber may be solidified. In the invention herein, solidification of a plasticized fiber is referred to as increasing the viscosity of said plasticized fiber. Generally, the viscosity of a plasticized fiber may be increased by at least two times during solidification. This includes, but is not limited to increasing the viscosity of said plasticized fiber by at least three times, or by at least four times, or by at least five times, or by at least six times, or by at least seven times, or by at least ten times, or by at least 20 times. In the extreme case, the viscosity of a solidified fiber is very large and may be considered "infinite". In this extreme case, the solidified fiber can be considered an "elastic" or "solid" material.

A plasticized fiber may be solidified by various ways. By way of example but not by way of limitation, depending on the composition of said plasticized fiber, solidification may be by evaporating solvent from said plasticized fiber, by cooling said plasticized fiber (e.g., by cooling said plasticized fiber to below its melting temperature, by cooling said plasticized fiber to below the melting temperature of a solvent it contains, etc.), or by cross-linking some of the constituents of said plasticized fiber.

To accelerate or control the rate at which solvent is evaporated, the apparatus herein may further comprise a unit for evaporating solvent from the deposited three dimensional structural framework. Such units for evaporating solvent include, but are not limited to devices (e.g., fans, fans including a heater, etc.) for blowing a gas (e.g., air, nitrogen, argon, $CO_2$, etc.) on and/or through a deposited three dimensional structural framework. Such units for evaporating solvent also include, but are not limited to drying ovens with temperature and/or pressure control, temperature-controlled stages or substrates, and so on.

Similarly, to accelerate or control the rate at which a deposited three dimensional structural framework is cooled, the apparatus herein may further comprise a unit for cooling a deposited three dimensional structural network. Such units include, but are not limited to temperature-controlled stages or substrates (e.g., low-temperature stages or substrates), devices (e.g., fans, etc.) for blowing cool gas or air (e.g., cryogenic air) on and/or through the fibrous structure, and so on.

Furthermore, for accelerating or controlling the rate at which solvent is removed from the fibrous structure, or for accelerating or controlling the cooling rate of the deposited three dimensional structural framework, in some embodiments the stage or substrate on which the three dimensional structural framework is deposited (e.g., the "deposition surface") may comprise a perforated plate or grid that is impermeable to a deposited fiber, but permits gas flow through it.

In some embodiments, therefore at least one stage on which fibers are deposited comprises a solid grid or a solid plate having one or more (e.g., one or a plurality of) perforations or holes or pores through which gas flows for cooling or freezing the deposited fibers or for evaporating solvent from said deposited fibers. Thus, in some embodiments the stage on which one or more fibers are deposited comprises a perforated plate (e.g., a solid, perforated plate, or a mesh, or a grid, or a "sieve").

In some embodiments, furthermore, an apparatus or method herein may further comprise a punching unit, or a cutting unit (including, for example, a blade), or a stamping unit, etc. to punch or trim or cut or stamp a dosage form or a drug-containing solid of desired shape and/or volume from (e.g., out of) a deposited or patterned three-dimensional structural framework.

In some embodiments of the apparatus or method herein, an extrusion channel further comprises at least one sensing port for attaching a sensor to the extruder channel walls. By way of example but not by way of limitation, said sensor may be selected from the group comprising pressure sensors, temperature sensors, flow rate sensors, sensors for measuring the composition of the material in the extrusion channel (e.g., by near infrared spectroscopy, Fourier transform infrared spectroscopy, nuclear magnetic resonance spectroscopy, raman spectroscopy, etc.), or sensors for determining the physical form of the material in the extrusion channel (e.g., by X-ray spectroscopy, Fourier transform infrared spectroscopy, nuclear magnetic resonance spectroscopy, raman spectroscopy, etc.), and others.

More specifically, in some embodiments, any apparatus or method herein may further comprise a pressure sensor for measuring the pressure of a plasticized matrix in an extrusion channel.

In some embodiments, moreover, the method or apparatus herein further comprises at least a force sensor for measuring the force and/or pressure applied on at least one piston during filling of a second extruder extrusion channel and/or for measuring the force and/or pressure applied on at least one piston while said piston advances towards a fiber fabrication exit port to extrude plasticized fiber through said exit port.

In some embodiments, a first extruder extrusion channel bifurcates into multiple exit ports, each exit port having a valve and at least two valves mated to the input ports of at least two second extruders, and wherein each second extruder comprises a translatable piston, and wherein at least two pistons of at least two second extruders are translatable by a single electric motor. Such embodiments are preferable because the number of electric motors can potentially be reduced as the apparatus is scaled up for producing more dosage forms faster.

EXPERIMENTAL EXAMPLES

Part 1

The following examples present ways by which the fibrous dosage forms may be prepared and analyzed, and will enable one of skill in the art to more readily understand the principle thereof. The examples are presented by way of illustration and are not meant to be limiting in any way.

Example 1.1: Apparatus for Preparing Fibrous Dosage Forms

Figure 15:
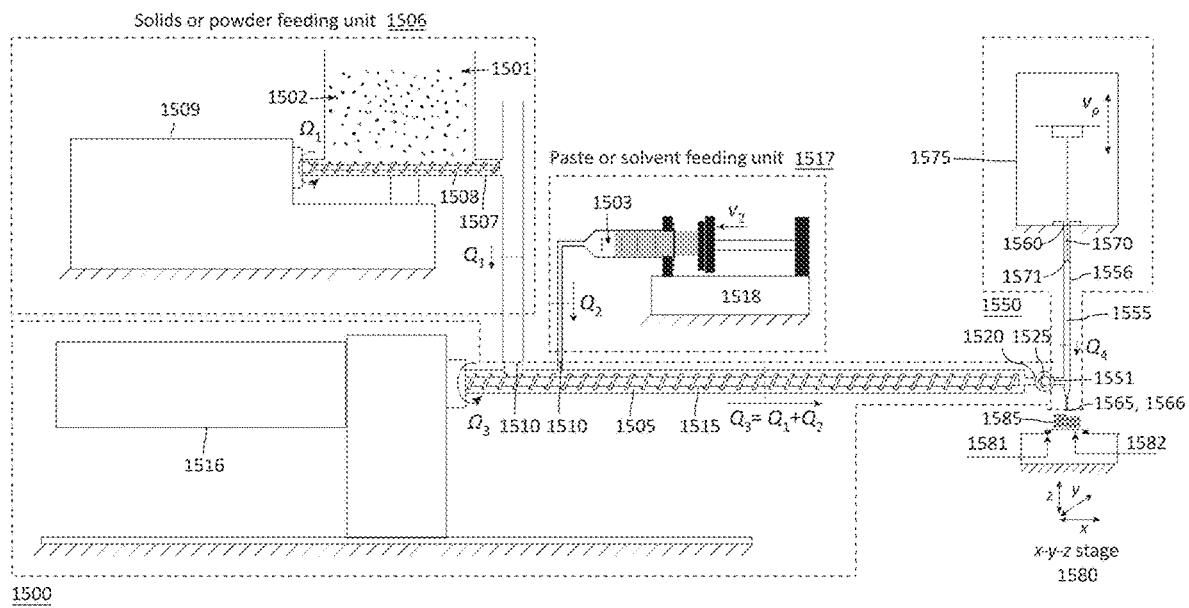
FIG. 15 shows a schematic of the non-limiting apparatus and method used to experimentally validate the apparatus and process, and prepare the experimental dosage forms herein.

The fibrous dosage forms were prepared using an apparatus as shown schematically in FIG. 15. The apparatus includes a powder feeding unit 1506 comprising a powder feeding extrusion channel 1507 and two intermeshing, co-rotating powder feeding screws 1508 (e.g., a co-rotatable "twin screw") driven by an electric motor 1509. The apparatus further includes a first extruder 1500 comprising an extrusion channel 1505 with feeding ports 1510 for injecting drug, excipient, and solvent into the extrusion channel 1505 and two intermeshing, co-rotating extrusion screws 1515 (e.g. again a co-rotatable twin-screw) driven by an electric motor 1516. The channel 1505 terminates at an exit port 1520. Said exit port 1520 has a check valve 1525 with cracking pressure 0.04 MPa (e.g., between 0.01 MPa and 100 MPa). The apparatus further includes a liquid or paste feeding unit 1517 comprising a positive displacement pump for dispensing liquids or pastes 1518 into the first extruder extrusion channel 1505 at a controlled flow rate.

The apparatus further includes at least a second extruder 1550. Said second extruder 1550 comprises its own extrusion channel 1555 defined by channel walls 1556, said channel walls 1556 having a composition comprising a glass (e.g., in the non-limiting experimental example herein the second extruder channel walls include a barrel of a glass syringe). The second extruder extrusion channel 1555 has an input port 1551 mated to said check valve 1525, and a closed first end 1560 and a second end 1565 terminating in a fiber fabrication exit port nozzle 1566. The second extruder extrusion channel 1555 (e.g., the cross sectional area (or radius) of the second extruder extruder channel 1555) further contracts or tapers down before the fiber fabrication exit port nozzle 1566 to the cross sectional area (or radius) of said fiber fabrication exit port nozzle 1566.

The second extruder channel walls 1556 are in contact with and enclose a piston 1570 translatable along the channel's 1555 longitudinal axis between said first end 1560 and said input port 1551. Said piston 1570 comprises a seal 1571 around its circumference to prevent or block flow of plasticized matrix through the first end 1560 of the second extruder extrusion channel 1555. The seal has a composition comprising a fluoropolymer (e.g., Teflon). The second extruder 1550 further comprises an electric motor 1575 for translating the piston 1570.

The apparatus further comprises a translating x-y-z stage 1580 comprising a plate or build platform attached to or connected to an assembly or stack of three linear stages. Each said linear stage is driven by a servo motor. Thus the position of the x-y-z stage can be controlled in the xy, and z directions, and the velocity or speed of the x-y-z stage can be controlled or maintained at the controlled velocity or speed of the extruded plasticized fiber. Moreover, the x-y-z stage (e.g. the plate or the build platform) includes a deposition surface for depositing and assembling fiber to form a three dimensional structural framework. Said deposition surface comprises a solid grid or mesh. The solid grid or mesh allows cryogenic air flow through it to cool the deposited three dimensional structural framework.

The apparatus further comprises a solvent evaporation unit. The solvent evaporation unit comprises a vacuum chamber connected to a vacuum pump. The apparatus further comprises a cutting unit for punching/cutting/trimming a drug-containing solid with desirable geometry from the deposited three dimensional structural framework. In the non-limiting experimental example the cutting unit comprises a round punch of diameter 13 mm and with sharp edges.

The screws of the powder feeder are intermeshing, co-rotating, and about 225 mm long. The outer diameter of the screw is 9 mm, the helix angle about 9°, the screw-channel height about 1.5 mm, and the channel width 4.5 mm.

The syringe barrel of the excipient-solvent paste feeding unit has an inner diameter of about 7.3 mm, and the syringe pump is driven by an electric servo motor that allows advancement of the piston at a precisely controlled speed.

The extrusion screw is 480 mm long, has an outer diameter of 12 mm, a helix angle of about 9°, a channel height of about 2 mm, and a channel width of 6 mm.

The syringe barrel (e.g., the second extruder extrusion channel) has a diameter of 1.15 mm. The syringe pump to advance the piston is driven by an electric servo motor that allows advancement of the piston at a precisely controlled speed.

The extrusion nozzle (e.g., the fiber fabrication exit port nozzle) comprises a needle of length 12 mm and an inner radius of 84.5 µm.

Example 1.2: Preparation of Fibrous Dosage Forms

The non-limiting materials used for preparing the dosage forms were as follows. Drug: Ibuprofen, received as solid particles of size about 25 µm from BASF, Ludwigshafen, Germany. Excipients: Hydroxypropyl methylcellulose with a molecular weight of 120 kg/mol (HPMC 120 k), and Methacrylic acid-ethyl acrylate copolymer (1:1) with a molecular weight of about 250 kg/mol (trade name: Eudragit L100-55, received from Evonik, Essen, Germany); Gastro-intestinal contrast agent: Barium sulfate ($Ba_2SO_4$), received as solid particles of size ~1 µm; Solvent: Dimethylsulfoxide (DMSO).

The as-received ibuprofen particles were loaded into the powder feeding unit without further processing. The other materials, HPMC 120 k, Eudragit L100-55, and Barium sulfate particles were mixed with DMSO at concentrations 64, 192, and 137 mg/ml to form a uniform viscous paste. The paste was loaded into the excipient-solvent paste feeding unit.

The apparatus was then operated as follows: The powder feeding screws were rotated and the piston of the excipient-solvent paste feeding unit was advanced. Concomitantly the extrusion screws were rotated to fill the second extruder extrusion channel while the piston of the second extruder was receded. As soon as the second extruder extrusion channel was adequately filled, the powder feeding screw rotation, the advancement of the paste feeding piston, the extruder screw rotation, and the motion of the second extruder piston were stopped. The second extruder piston was then advanced to extrude fiber through the fiber fabrication exit port nozzle. The speed of the extruded fiber was about 10 mm/s. The extruded fiber was then deposited or micro-patterned in a cross-ply arrangement with nominal inter-fiber distance, $\lambda_n=650$ µm. During micro-patterning, the stage was moved at roughly the same speed as that of the extruded fiber, about 10 mm/s. Moreover, during micro-patterning, cold or cryogenic air at a temperature of −5° C. and a velocity of about 10 cm/s was blown through the perforated stage and the patterned structure to cool the fibers and freeze the structure.

Eventually, as the second extruder piston reached the input port of the second extruder extrusion channel, said second extruder channel was refilled by the mixture in the first extruder. The cycle of filling the second extruder channel and micropatterning fiber from the second extruder channel onto the stage was repeated until the required quantity of fiber mass was patterned. After patterning, the patterned structure was brought into a vacuum chamber to evaporate the solvent. Finally, the dosage form or drug-containing solid was punched out from the patterned material.

Example 1.3: Determination of the Powder Flow Rate into the Extruder

As-received ibuprofen particles were loaded into the powder feeding unit without further processing. The powder feeding screws were then rotated at a specific rotation rate for 30-180 seconds, and the mass of the dispensed powder was determined with an analytical balance (Mettler Toledo). For determining the powder flow rate, the dispensed powder mass was divided by the density of solid ibuprofen (1030 kg/m$^3$) and the feeding time (30-180 s). The powder flow rate was determined for six screw rotation rates.

Figure 16:
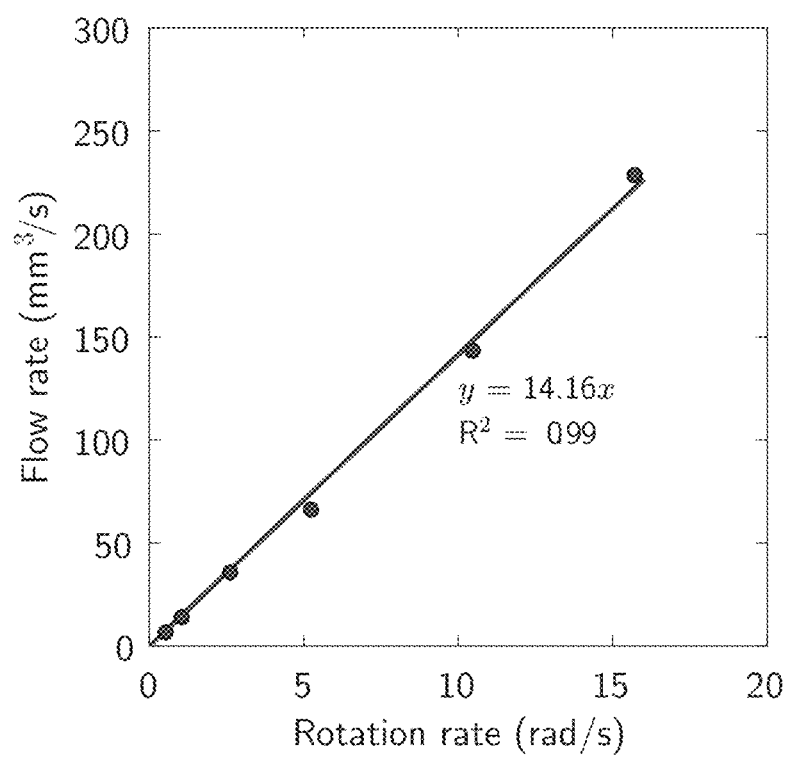
FIG. 16 presents non-limiting experimental data of the feeding rate by the powder feeding unit versus rotation rate of the powder feeding screws.

FIG. 16 is a plot of the volumetric powder flow rate versus rotation rate of the powder feeding screws. The powder flow rate, $Q_1$, increased linearly with rotation rate, $\Omega_1$. The fit equation, $Q_1=14.16\,\Omega_1$ mm$^3$/s, and the $R^2$ value was 0.99. Thus, the deviation from linearity was very small.

Moreover, from section "Process models", under the assumptions that (a) the flow rate by the twin-screw feeder is twice that by a single screw, (b) the velocity profile of the powder bed in the screw channel is linear, as in Couette flow, and (c) the screw channel cross section is rectangular, the powder flow rate is:

$$Q_1 = \varphi_{part} H_1 W_1 \Omega_1 R_1 \cos(\theta) \qquad (16)$$

where $\varphi_{part}$ the volume fraction of particles in the powder bed, $H_1$ the height and $W_1$ the width of the screw channel, $R_1$ is the outer radius of the screw (inner radius of the barrel), $\Omega_1$ the angular velocity of the screw with respect to the barrel, and $\theta$ the helix angle of the screw.

Substituting the relevant parameters, $\varphi_{part}\approx 0.5$, $H_1=1.5$ mm, $W_1=4.5$ mm, $R_1=4.5$ mm, and $\theta=9°$, by Eq. (1) the flow rate, $Q_1=14.44\,\Omega_1$ mm³/s. This is very close to the measured rate, which validates the model. Thus, the powder flow rate into the first extruder was both repeatable and predictable.

Example 1.4: Determination of the Flow Rate of Drug-Excipient-Solvent Paste Through the Extruder The first extruder was fed with drug powder and excipient-solvent paste as in Experimental example 1.2. The second extruder, however, was replaced by a 5 ml syringe which was mated to the check valve at the first extruder's exit. The extruder screws were then rotated at a specific rotation rate until 4 ml of drug-excipient-solvent paste was filled into the syringe. The time required to fill the syringe was recorded for a screw rotation rate of 20 rotations per minute. The flow rate at the specific screw rotation rate was determined by dividing 4 ml with the time to fill the syringe.

In the experiments, at 20 rotations/min the 4 ml syringe was filled in a few seconds.

Example 1.5: Determination of the Forces Acting on the Syringe Pistons to Co-Extrude Fiber Core and Coating A load cell (FX1901 force sensor, Variohm Eurosensor, Towcester, UK) was placed between the piston of the second extruder and the electric motor actuating said piston to measure the force acting on the piston while fiber was extruded and micro-patterned. The force was measured for various velocities (or flow rates) of the piston.

Figure 17:
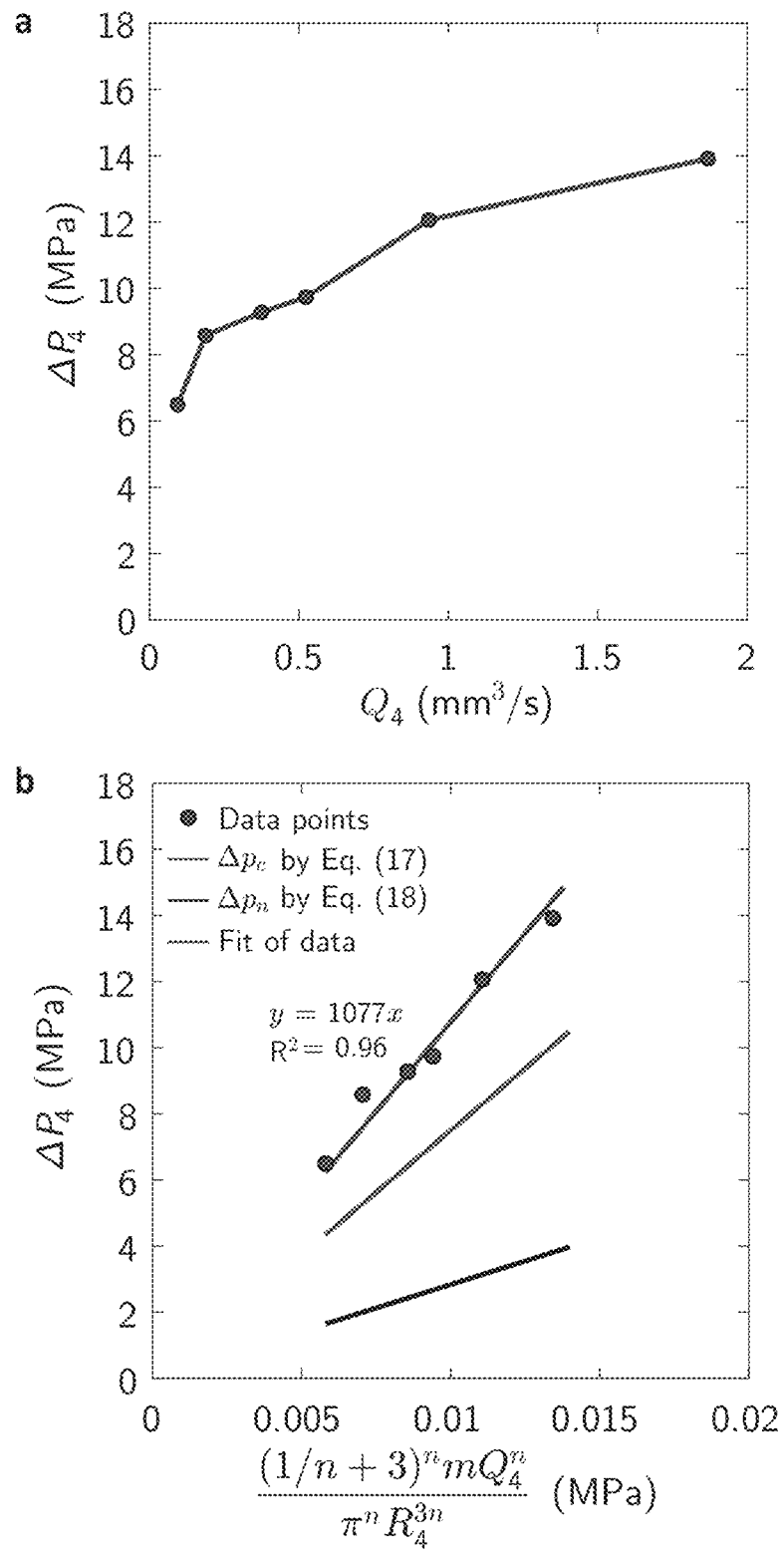
FIG. 17 presents non-limiting experimental data of the pressure acting on the piston of the second extruder versus flow rate through the fiber fabrication port.

FIG. 17a plots the pressure acting on the piston to extrude plasticized matrix through the fiber fabrication exit port nozzle versus flow rate. The pressure increased with flow rate at a rate slightly less than linear. The pressure drop was about 14 MPa at a flow rate slightly less than 2 mm³/s.

Generally, the pressure gradient along the second extruder extrusion channel should be greatest when the channel radius contracts or tapers down (e.g., from the radius of the piston to the radius of the fiber fabrication exit port nozzle) or when the radius is smallest (e.g., along the fiber fabrication exit port nozzle).

Adapting the prior work, for a non-Newtonian power-law fluid the pressure drop across a contraction may be written as:

$$\Delta p_c = \frac{(1/n+3)^n m K_4 Q_4^n}{4\pi^n R_4^{3n}} \tag{17}$$

where m is a constant of dimension Pa·s$^n$ and n a dimensionless constant describing the viscosity of the extruded paste, $K_4$ is a constant specific to the geometry of the contraction, and $R_4$ is the radius of the fiber fabrication exit port nozzle. The pressure drop along the fiber fabrication exit port nozzle may be approximated by:

$$\Delta p_n = \frac{2(1/n+3)^n m Q_4^n L_4}{\pi^n R_4^{3n+1}} \tag{18}$$

where $L_4$ is the length of the fiber fabrication exit port nozzle. Combining Eqs. (17) and (18), the pressure drop across the entire system (e.g., the second extruder extrusion channel) may approximated as:

$$\Delta p = \frac{(1/n+3)^n m Q_4^n}{\pi^n R_4^{3n}}\left(\frac{K}{4} + \frac{2L}{R}\right) \tag{19}$$

As suggested by Eq. (19), FIG. 17b plots the measured pressure drop across the entire system versus $(1/n+3)mQ_4^n/\pi^n R^{3n}$. Indeed, the data followed an equation of the form:

$$\Delta p = k_1 \frac{(1/n+3)^n m Q_4^n}{\pi^n R_4^{3n}} \tag{20}$$

where $k_1$ is a constant.

Combining Eqs. (19) and (20) gives:

$$k_1 = \frac{K}{4} + \frac{2L}{R} \tag{21}$$

From the fit equation to the data shown in FIG. 17b, $k_1=1077$. Thus, further using $L_4=12$ mm and $R_4=84.5$ μm, the experimentally-derived K~3000. This value is of the order of previously reported values, ~$10^3$.

FIG. 17b further plots the calculated pressure drops by Eqs. (17) and (18) across the contraction and the fiber fabrication exit port nozzle for the relevant parameters. The calculated pressure drop across the contraction is about three times greater than that across the nozzle. Thus, it is expected that the pressure drop across the system could be decreased greatly by appropriate design of the contraction. A contraction comprising a taper in the second extruder extrusion channel having a taper angle no greater than 45 degrees or preferably no greater than 30 degrees may reduce the pressure drop across the contraction substantially.

Example 1.6: Microstructures of Micro-Patterned Dosage Forms

The microstructures of the fibrous dosage forms were imaged by a Zeiss Merlin High Resolution SEM with a GEMINI column. The top surfaces were imaged after coating the sample with a 10-nm thick layer of gold. The cross-sections were imaged after the sample was cut with a thin blade (MX35 Ultra, Thermo Scientific, Waltham, Mass.) and coated with gold as above. The specimens were imaged with either an in-lens secondary electron or a backscattered electron detector, at an accelerating voltage of 5 kV, and a probe current of 95 pA.

Figure 18:
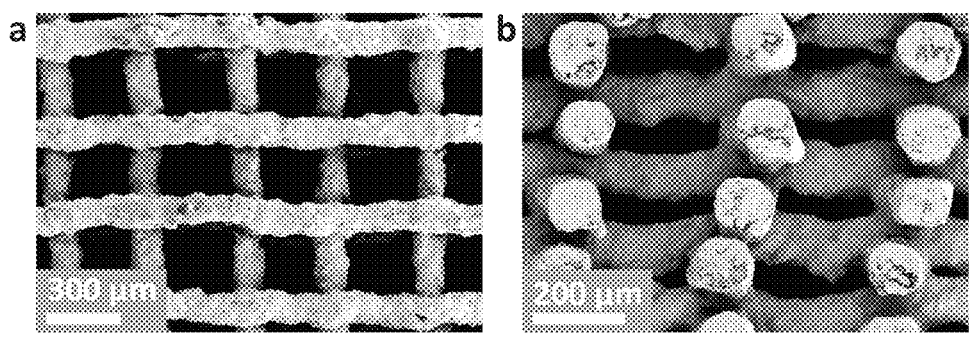
FIG. 18 shows scanning electron micrographs of (a) top view and (b) cross section of the microstructure of non-limiting experimental dosage forms prepared by an apparatus and method disclosed herein.

FIGS. 18a and 18b present scanning electron micrographs of the top and front views of the dosage form. The dosage form consisted of a cross-ply structure with contiguous void space. The solid fiber radius, $R_0$, was 59 μm, and the inter-fiber spacing, $\lambda_0$, was 365 μm, Table 1.

From prior work, if the wet structure contracts isotropically during solvent evaporation, the microstructural parameters of the solid, cross-ply structure may be calculated from the nominal parameters of the wet, 3D-printing or 3D-micropatterning or deposition process as:

$$\frac{R_0}{R_n} = \frac{\lambda_0}{\lambda_n} = \left(1 - \frac{c_{solv}}{\rho_{solv}}\right)^{1/3} \quad (22)$$

where $R_n$ is the nominal radius and $\lambda_n$ the nominal inter-fiber spacing of the wet, patterned structure, $c_{solv}$ is the concentration of solvent in the wet fiber, and $\rho_{solv}$ is the density of the solvent. For the relevant parameters listed in the legends of Table 1, by Eq. (22) the calculated $R_0=54$ μm, and the calculated $\lambda_0=422$ μm. These values agree with the measured values listed in Table 1; both $R_0$ and $\lambda_0$ were predictable from the nominal process parameters.

Moreover, the volume fraction of fibers in the dosage forms, $\varphi_f$, may be calculated by:

$$\varphi_f = \xi \frac{\pi R_0}{2\lambda_0} \quad (23a)$$

where $\xi$ is the ratio of the thicknesses of the dosage form without and with flattened fiber-to-fiber contacts $$\xi = R_0 n_{layers}/H_0 \quad (23b)$$

Here $n_{layers}$ is the number of stacked layers and $H_0$ the half-thickness of the solid dosage form or drug-containing solid. For the relevant parameters listed in Table 1, $\varphi_f=0.34$.

TABLE 1

Microstructural parameters of the fibrous dosage forms.

| | $R_0$ (μm) | $\lambda_0$ (μm) | $\varphi_f$ |
|---|---|---|---|
| Uncoated | 59 | 365 | 0.34 |

$R_0$: fiber radius;
$\lambda_0$: inter-fiber distance;
$\varphi_f$: volume fraction of fibers.
$R_0$ and $\lambda_0$ were obtained from FIG. 18.
The volume fractions were obtained from Eq. (23).
The nominal process parameters were: $R_n = 84$ μm, $\lambda_n = 650$ μm (uncoated), $c_{solv} = 800$ g/ml, and $\rho_{solv} = 1100$ g/ml.
Moreover, the half-thickness of the dosage form, $H_0 = 2.5$ mm and $n_{layers} = 60$.

Example 1.7: Viscosity of Drug-Excipient Solvent Paste (i.e., the Wet Fibers)

The shear viscosity of the drug-excipient-solvent paste (e.g., the viscosity of the extruded plasticized matrix or fiber for preparing the non-limiting experimental dosage forms) was determined by a shear rheometer (Anton Paar MCR 302 Rheometer) equipped with a 25 mm diameter cone. The temperature was 20° C., and the shear strain-rate was in the range 0.01-100/s during the experiments.

Figure 19:
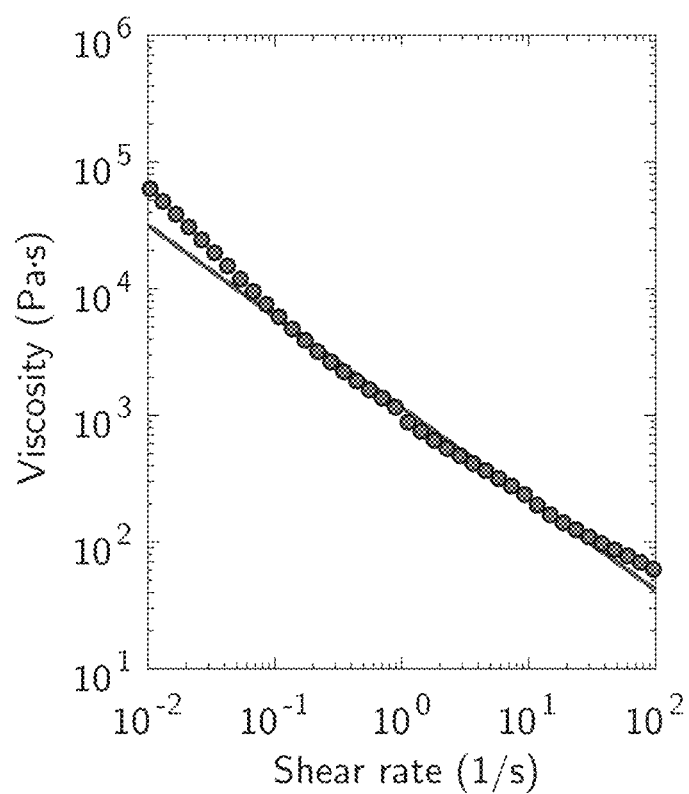
FIG. 19 is a plot of shear viscosity versus shear rate of a non-limiting plasticized matrix used for preparing experimental dosage forms by the disclosed apparatus and method.

FIG. 19 is a plot of the shear viscosity versus shear rate. The viscosity followed a power law function of the form:

$$\mu = m\dot{\gamma}^{n-1} \quad (24)$$

where m is a constant of dimension Pa·$s^n$ and n a dimensionless constant. From the fit in FIG. 19, m=1150 Pa·$s^n$ and n=0.28.

Experimental Examples

Part 2

The following examples present additional ways by which the fibrous dosage forms may be prepared and analyzed, and will enable one of skill in the art to more readily understand the principle thereof. The examples are presented by way of illustration and are not meant to be limiting in any way.

Example 2.1: Preparation of Fibrous Dosage Forms

The non-limiting materials used for preparing the dosage forms were as follows. Drug: Ibuprofen, received as solid particles from BASF, Ludwigshafen, Germany. Excipient: A mixture of 67 wt % hydroxypropyl methylcellulose with a molecular weight of 10 kg/mol (HPMC 10 k), and 33 wt % polyoxyl stearate (also referred to herein as "POS"; Tradename: Gelucire 48/16, Gattefosse). Solvent: Dimethylsulfoxide (DMSO).

The fibrous dosage forms were prepared as follows. The as-received ibuprofen drug particles were first dissolved in DMSO at a concentration of 123 mg drug/ml DMSO. The solution was then combined with the excipient at a concentration of 1.11 g excipient/ml DMSO. The mixture was fed into a first extruder and extruded through said first extruder to form a uniform, viscous paste.

The paste was then filled in a second extruder (e.g., a glass syringe with a hypodermic needle at the syringe exit and with a translatable piston driven by a syringe pump). The paste was extruded through said hypodermic needle by advancing the piston at a controlled speed with said syringe pump. The extruded wet fiber (nominal radius, $R_n=130$ μm) was then patterned on a moving stage to form a wet fibrous dosage form with cross-ply structure. Three dosage form structures (A, B, and C) with nominal inter-fiber spacing, $\lambda_n=900$, 500, and 385 μm, were patterned, as listed in Table 2. After patterning, warm air at a temperature of about 50° C. and a velocity of 2.3 m/s was blown on the dosage form to evaporate the solvent and solidify the structure.

The solid dosage forms consisted of 10 wt % ibuprofen, 60 wt % HPMC 10 k, and 30 wt % POS.

Example 2.2: Microstructures of Fibrous Dosage Forms

The fibrous dosage forms were imaged by a Zeiss Merlin High Resolution SEM with a GEMINI column. Top views were imaged without any preparation of the sample. For imaging cross-sections, however, the samples were cut with a thin blade (MX35 Ultra, Thermo Scientific, Waltham, Mass.). Imaging was done with an in-lens secondary electron detector. The accelerating voltage was 5 kV and the probe current was 95 pA.

Figure 20:
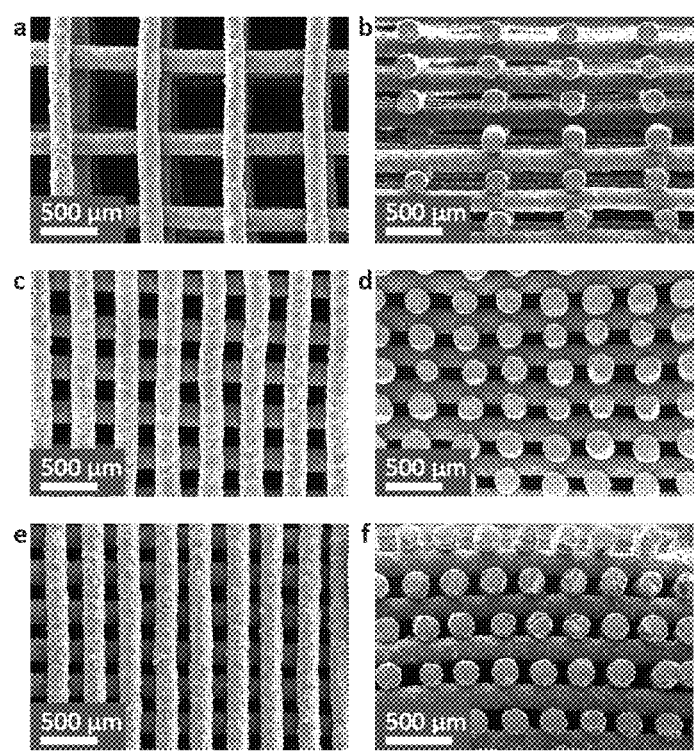
FIG. 20 presents additional scanning electron micrographs of microstructures of dosage forms prepared by an apparatus and method disclosed herein.

Scanning electron micrographs of the fibrous dosage forms are shown in FIG. 20. FIG. 20a is the top view and FIG. 20b the front view of dosage form A. The measured radius, $R_0=98$ and the inter-fiber distance, $\lambda_0=712$ μm. This is 75-79 percent of the nominal values, $R_n=130$ μm and $\lambda_n=900$ μm. FIGS. 20c-20f show the microstructures of the other dosage forms. The ratios $R_0/R_n=\lambda_0/\lambda_n=0.75$-0.8, Table 2. Thus, for all dosage forms the normalized contraction due to drying was about the same, and isotropic. Moreover, the standard deviations of $R_0$ and $\lambda_0$ were small: the fiber extrusion and deposition process (e.g., the patterning process) was well controlled.

TABLE 2

Microstructural parameters of fibrous dosage forms.

|   | $R_0$ (μm) | $R_0/R_n$ | $\lambda_0$ (μm) | $\lambda_0/\lambda_n$ | $R_0/\lambda_0$ |
|---|---|---|---|---|---|
| A | 98 ± 3 | 0.75 | 712 ± 45 | 0.79 | 0.14 |
| B | 104 ± 4 | 0.80 | 385 ± 15 | 0.77 | 0.27 |
| C | 97 ± 2 | 0.75 | 297 ± 20 | 0.77 | 0.33 | the nominal values $R_n$=130 μm, and $\lambda_n$=900, 500, and 385 μm, respectively, for dosage forms A, B, and C.

The data are obtained from the SEM images in FIG. 20.

We claim:

1. A method of manufacturing pharmaceutical solid dosage forms comprising the steps of:
feeding at least one of each active ingredient, excipient, and solvent into the extrusion channel of at least one first extruder, said channel terminating at at least one exit port, said exit port having at least a valve, said valve mated to at least one input port of at least one second extruder; mixing the active ingredient, excipient, and solvent to form a plasticized matrix; conveying said plasticized matrix to said first extruder's at least one exit port using at least a rotatable screw;

extruding the conveyed plasticized matrix through said exit port and valve, thereby filling at least one extrusion channel of at least one second extruder with said extruded plasticized matrix, said second extruder channel terminating at at least one fiber fabrication exit port; extruding the plasticized matrix in said second extruder extrusion channel through said fiber fabrication exit port at a controlled speed using an advancing piston; and depositing plasticized fiber extruded from said second extruder onto a fiber assembling stage to form a three dimensional fiber structural framework defined by the motion of said stage at the speed of the exiting, extruded plasticized fiber; wherein the three dimensional fiber structural framework is used in a pharmaceutical solid dosage form.

2. The method of claim 1, wherein at least one valve allows flow of plasticized matrix from a first extruder extrusion channel through an exit port of said first extruder and into the channel of a second extruder while said second extruder extrusion channel is filled with plasticized matrix.

3. The method of claim 1, wherein at least one valve blocks flow of plasticized matrix from the channel of a second extruder through an exit port of a first extruder while fiber is extruded through a fiber fabrication exit port of said second extruder extrusion channel.

4. The method of claim 1, wherein at least one valve comprises a check valve permitting flow of plasticized matrix from said first extruder channel into said second extruder channel, and blocking flow from said second extruder channel into said first extruder channel.

5. The method of claim 1, further comprising removably attaching a movable solid surface to a fiber fabrication exit port to block flow of plasticized matrix through said fiber fabrication exit port during filling.

6. The method of claim 1, further comprising moving a movable solid surface away from a fiber fabrication exit port to allow flow of plasticized matrix through said fiber fabrication exit port.

7. The method of claim 5, wherein a movable solid surface is included in or attached to a fiber assembling stage.

8. The method of claim 1, wherein at least one valve comprises a three-way valve.

9. The method of claim 1, wherein at least one valve comprises a three-way valve, and wherein said three-way valve comprises a flow path permitting flow of plasticized matrix from said first extruder channel into said second extruder channel while blocking flow of plasticized matrix from said first extruder channel towards a fiber fabrication exit port of said second extruder channel.

10. The method of claim 1, further comprising blocking flow of plasticized matrix through a fiber fabrication exit port during filling using a second valve, said second valve positioned between an input port of the second extruder extrusion channel and said fiber fabrication exit port.

11. The method of claim 1, wherein a second valve blocks flow of plasticized matrix from a first extruder extrusion channel to an exit port of a second extruder extrusion channel while said second extruder extrusion channel is filled with plasticized matrix.

12. The method of claim 1, further comprising flexibly blocking flow of plasticized matrix through a fiber fabrication exit port using a second valve, and wherein said second valve allows flow of plasticized matrix through a channel of a second extruder and through a fiber fabrication exit port of said second extruder extrusion channel while fiber is extruded through said fiber fabrication exit port.

13. The method of claim 1, wherein one or more rotatable screws are used for forming and extruding plasticized matrix in the first extruder extrusion channel.

14. The method of claim 1, wherein the advancing piston is in contact with and enclosed by said second extruder extrusion channel.

15. The method of claim 1, wherein the piston is driven by an electric motor.

16. The method of claim 1, wherein a cross sectional area of a second extruder extrusion channel is in the range between 0.001 cm$^2$ and 50 cm$^2$.

17. The method of claim 1, wherein a second extruder extrusion channel comprises no more than one fiber fabrication exit port.

18. The method of claim 1, wherein plasticized matrix in a second extruder extrusion channel is extruded through a fiber fabrication port of said second extruder extrusion channel at a controlled speed using an advancing piston in contact with and enclosed by said second extruder extrusion channel, and wherein said piston comprises a seal around its circumference to block or restrict flow of plasticized matrix through the first end of said second extruder extrusion channel.

19. The method of claim 1, wherein a fiber fabrication exit port is designed to extrude fibrous extrudate with a fiber thickness no greater than 2 mm.

20. The method of claim 1, wherein the first extruder extrusion channel bifurcates into multiple exit ports.

21. The method of claim 1, wherein the viscosity of an extruded, exiting plasticized fiber is in the range between 10 Pa·s and 100,000 Pa·s at a shear rate of 1/s.

22. A method of manufacturing pharmaceutical solid dosage forms comprising the steps of: feeding at least one of each active ingredient and excipient into the extrusion channel of at at least one first extruder, said channel terminating at least one exit port, said exit port having at least a valve, said valve mated to at least one input port of at least one second extruder;

mixing and heating the active ingredient and excipient to form a plasticized matrix; conveying said plasticized matrix to said first extruder's exit port using at least a rotatable screw;

extruding the conveyed plasticized matrix through said exit port and valve, thereby filling at least one extrusion channel of at least one second extruder with said extruded plasticized matrix, said second extruder channel terminating at at least one fiber fabrication exit port;

extruding the plasticized matrix in said second extruder extrusion channel through said fiber fabrication port at a controlled speed using an advancing piston driven by an electric motor; and depositing the extruded plasticized fiber onto a fiber assembling stage to a form a three dimensional fiber structural framework defined by the motion of said stage at the speed of the exiting extruded, plasticized fiber;

wherein the three dimensional fiber structural framework is used in a pharmaceutical solid dosage form.

23. A method of manufacturing pharmaceutical solid dosage forms comprising the steps of:

feeding at least one of each active ingredient, excipient, and solvent into the extrusion channel of at least one first extruder, said channel terminating at at least one exit port, said exit port having at least a check valve, and said at least one exit port mated to at least one input port of at least one second extruder; mixing the active ingredient, excipient, and solvent to form a plasticized matrix; conveying said plasticized matrix to said first extruder's exit port using at least a rotatable screw; extruding the conveyed plasticized matrix through said exit port, thereby filling at least one extrusion channel of at least one second extruder with said extruded plasticized matrix, said second extruder channel terminating at at least one fiber fabrication exit port;

extruding the plasticized matrix in said second extruder extrusion channel through said fiber fabrication exit port at a controlled speed using an advancing piston driven by an electric motor;

and depositing the extruded plasticized fiber onto a fiber assembling stage to a form a three dimensional fiber structural framework defined by the motion of said stage at the speed of the exiting extruded, plasticized fiber; wherein the three dimensional fiber structural framework is used in a pharmaceutical solid dosage form.

* * * * *